(12) United States Patent
Janek et al.

(10) Patent No.: US 8,684,966 B2
(45) Date of Patent: Apr. 1, 2014

(54) SAFETY MEDICAL SYRINGE WITH RETRACTABLE NEEDLE

(75) Inventors: Gregory A. Janek, Conover, OH (US); Vincent Runfola, Apopka, FL (US); Li Xian Yu, Zhejiang (CN)

(73) Assignee: Midland Medical Devices Holdings, LLC, Midland, TX (US)

( * ) Notice: Subject to any disclaimer, the term of this patent is extended or adjusted under 35 U.S.C. 154(b) by 228 days.

(21) Appl. No.: 12/924,424

(22) Filed: Sep. 27, 2010

(65) Prior Publication Data

US 2011/0021989 A1    Jan. 27, 2011

Related U.S. Application Data

(63) Continuation of application No. 11/249,741, filed on Oct. 14, 2005, now Pat. No. 7,803,132.

(60) Provisional application No. 60/618,137, filed on Oct. 14, 2004, provisional application No. 60/626,916, filed on Nov. 12, 2004, provisional application No. 60/657,700, filed on Mar. 3, 2005.

(51) Int. Cl.
 *A61M 5/50* (2006.01)

(52) U.S. Cl.
 USPC .......................................................... 604/110

(58) Field of Classification Search
 USPC .......... 604/110, 192, 220, 187, 311, 218, 195
 See application file for complete search history.

(56) References Cited

U.S. PATENT DOCUMENTS

| | | | | |
|---|---|---|---|---|
| 3,973,554 A * | 8/1976 | Tipton | | 600/5 |
| 4,955,870 A * | 9/1990 | Ridderheim et al. | | 604/195 |
| 4,994,034 A * | 2/1991 | Botich et al. | | 604/110 |
| 5,053,010 A * | 10/1991 | McGary et al. | | 604/110 |
| 5,085,640 A * | 2/1992 | Gibbs | | 604/110 |
| 5,180,369 A * | 1/1993 | Dysarz | | 604/110 |
| 5,180,370 A * | 1/1993 | Gillespie | | 604/110 |
| 5,211,629 A * | 5/1993 | Pressly et al. | | 604/110 |
| 5,328,484 A * | 7/1994 | Somers et al. | | 604/195 |
| 5,385,551 A * | 1/1995 | Shaw | | 604/110 |
| 5,407,436 A * | 4/1995 | Toft et al. | | 604/195 |
| 5,935,104 A * | 8/1999 | Janek et al. | | 604/110 |
| 5,984,898 A * | 11/1999 | Garvin | | 604/195 |
| 6,036,674 A * | 3/2000 | Caizza et al. | | 604/195 |
| 6,096,005 A * | 8/2000 | Botich et al. | | 604/110 |
| 6,099,500 A * | 8/2000 | Dysarz | | 604/110 |
| 6,179,812 B1 * | 1/2001 | Botich et al. | | 604/110 |
| 6,228,054 B1 * | 5/2001 | Dysarz | | 604/110 |
| 6,241,707 B1 * | 6/2001 | Dysarz | | 604/110 |

(Continued)

*Primary Examiner* — Emily Schmidt
*Assistant Examiner* — Michael J Anderson
(74) *Attorney, Agent, or Firm* — Robert C. Klinger

(57) ABSTRACT

A syringe includes a hollow barrel, a hollow plunger movable within the barrel and a needle assembly secured within and at a distal end of the barrel. The needle assembly includes a needle holder, a resilient member that biases the needle holder toward the proximal end opening of the barrel, and a retaining member releasably secured to the needle holder via a reduced material section. The retaining member maintains the needle holder at the distal end of the barrel against the bias of the resilient member. When the plunger is fully depressed within the barrel, the plunger engages the needle holder such that the retaining member is forced to break away and separate from the needle holder along the reduced material section to facilitate retraction of the needle holder and a needle secured to the needle holder into the retraction cavity disposed within the plunger.

20 Claims, 25 Drawing Sheets

(56) References Cited

U.S. PATENT DOCUMENTS

| | | | |
|---|---|---|---|
| 6,409,701 B1 * | 6/2002 | Cohn et al. | 604/110 |
| 6,413,237 B1 * | 7/2002 | Caizza et al. | 604/110 |
| 6,432,087 B1 * | 8/2002 | Hoeck et al. | 604/181 |
| 6,558,357 B1 * | 5/2003 | Hoeck | 604/195 |
| 6,585,690 B1 * | 7/2003 | Hoeck et al. | 604/110 |
| 6,599,268 B1 * | 7/2003 | Townsend et al. | 604/110 |
| 6,679,863 B2 * | 1/2004 | Bush et al. | 604/181 |
| 6,689,106 B2 * | 2/2004 | Bush et al. | 604/181 |
| 6,872,194 B2 * | 3/2005 | Doyle et al. | 604/192 |
| 7,090,656 B1 * | 8/2006 | Botich et al. | 604/110 |
| 2001/0053886 A1 * | 12/2001 | Caizza | 604/110 |
| 2002/0193736 A1 * | 12/2002 | Kiehne | 604/110 |
| 2003/0023205 A1 * | 1/2003 | Botich et al. | 604/110 |
| 2004/0116857 A1 * | 6/2004 | Kiehne | 604/110 |
| 2004/0167476 A1 * | 8/2004 | Westbye | 604/192 |
| 2005/0054980 A1 * | 3/2005 | Targell | 604/110 |
| 2006/0189935 A1 * | 8/2006 | Janek et al. | 604/110 |
| 2006/0258984 A1 * | 11/2006 | Kiehne | 604/110 |

* cited by examiner

SAFETY MEDICAL SYRINGE WITH RETRACTABLE NEEDLE

CROSS REFERENCE TO RELATED APPLICATIONS

This application is a continuation of prior U.S. application Ser. No. 11/249,741 entitled "SAFETY MEDICAL SYRINGE WITH RETRACTABLE NEEDLE" filed Oct. 14, 2005 now U.S. Pat. No. 7,803,132 B2 and claims priority from U.S. Provisional Patent Application Ser. No. 60/618,137, entitled "Safety Medical Syringe With Retractable Needle", and filed Oct. 14, 2004, U.S. Provisional Patent Application Ser. No. 60/626,916, entitled "Safety Medical Syringe With Retractable Needle", and filed Nov. 12, 2004, and U.S. Provisional Patent Application Ser. No. 60/657,700, entitled "Safety Medical Syringe With Retractable Needle", and filed Mar. 3, 2005. The disclosures of these patent applications are incorporated herein by reference in their entireties.

BACKGROUND OF THE INVENTION

1. Field of the Invention

The present invention pertains to safety medical syringes and, in particular, to syringes including a needle that retracts and is limited to a single use.

2. Description of the Related Art

Retractable syringes have become extremely increasingly important and desirable for use in hospitals and medical facilities for a number of reasons. In particular, retractable syringes are typically limited to a single use, where the hypodermic needle of the syringe is withdrawn into the syringe after aspiration and injection of a fluid, thus preventing multiple uses of the syringe and the potential transmission of human immunodeficiency virus (HIV) as well as other diseases from patient-to-patient. The retraction of the needle within the syringe after use also shields the needle and, prevents inadvertent needle jabs or pricks from occurring to patients and health care providers.

A variety of different retractable syringe devices have been designed to effectively withdraw the needle within the syringe after use. However, the challenge exists to design a retractable syringe that is limited to a single use yet is simplistic in design and assembly, such that the syringe can be produced on a large production scale while minimizing manufacturing costs.

SUMMARY OF THE INVENTION

An object of the present invention is to provide a retractable syringe that is simple to use and is non-reusable.

Another object of the present invention is to provide a retractable syringe that is simple in design and inexpensive to manufacture.

The aforesaid objects are achieved individually and in combination, and it is not intended that the present invention be construed as requiring two or more of the objects to be combined unless expressly required by the claims attached hereto.

In accordance with the present invention, a syringe comprises a hollow barrel including an opening at a proximal end of the barrel, an opening at a distal end of the barrel and a fluid chamber disposed within the barrel, and a hollow plunger extending into the barrel via the proximal end opening and axially movable within the barrel toward and away from the distal end opening, where the plunger includes an end wall that is releasably secured to the plunger at an opening disposed at a distal end of the plunger and is moved from the plunger distal end opening during use of the syringe to facilitate access to a retraction cavity disposed within the plunger. The syringe further includes a needle assembly secured within and at a distal end of the barrel. The needle assembly includes a needle holder, a resilient member that biases the needle holder toward the proximal end opening of the barrel, and a retaining member releasably secured to the needle holder via a reduced material section, where the needle holder includes a connector to secure a needle to the needle holder so as to permit the needle to extend through the distal end opening of the barrel.

The retaining member maintains the needle holder at the distal end of the barrel against the bias of the resilient member and, when the plunger is fully depressed within the barrel, the plunger is configured to engage the needle holder such that the end wall of the plunger is forced within the plunger and the retaining member is forced to break away and separate from the needle holder along the reduced material section to facilitate retraction of the end wall, the needle holder and a needle secured to the needle holder into the retraction cavity.

In an exemplary embodiment, the plunger end wall comprises a plug that frictionally engages with the plunger at the plunger distal end opening and, upon depression of the plunger toward the barrel distal end, the plug is configured to engage with the needle holder to dislodge the plug from the plunger and facilitate retraction of the plug, needle holder and needle secured to the needle holder into the retraction cavity.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION

Figure 1:
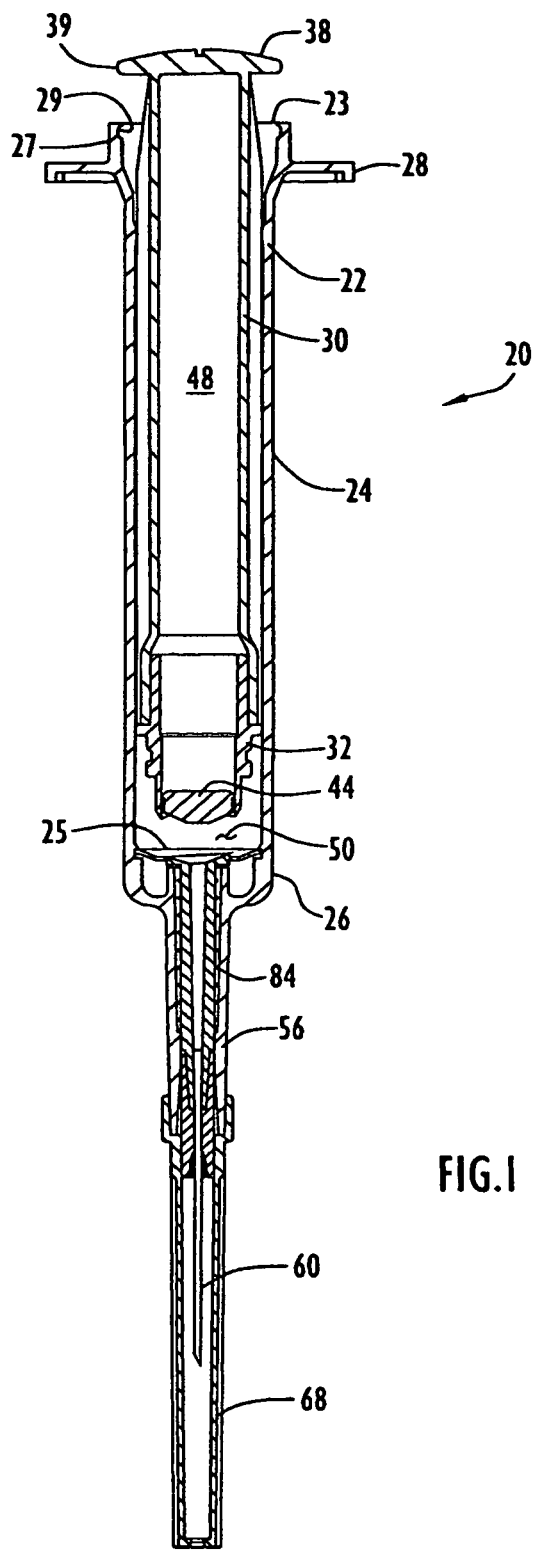
FIG. 1 is a side view in cross-section of a syringe in accordance with an embodiment of the present invention, where the needle extends from the syringe barrel and the syringe is ready for use.

Referring to FIG. 1, a medical syringe 20 includes a hollow cylindrical barrel 22 with an opening 23 at its proximal end, suitably dimensioned to receive a hollow plunger 30, and an opening at its distal end to permit exposure of a needle 60 from the syringe. The barrel 22 includes a main body portion 24 that receives and retains a portion of the plunger 30 and a distal end extension 26 of reduced internal diameter in relation to the main body portion 24 that receives a needle assembly 56 as described below. The plunger 30 includes a resilient seal 32 encircling the plunger near its distal end. A fluid cavity 50 is defined within the barrel 22 between the resilient seal 32 and other distal end portions of the plunger and a distal end 25 of the barrel main body portion 24, where the fluid cavity varies in volume based upon axial displacements of the plunger with respect to the barrel. A sheath 68 is removably securable to the distal end of the barrel 22 to enclose a needle 60 secured within the barrel as described below prior to use of the syringe. The barrel, plunger, resilient seal, sheath and all other components of the syringe may be constructed of any suitable medical grade materials (e.g., plastics and/or stainless steels) that facilitate operability of the syringe as described below.

Figure 6:
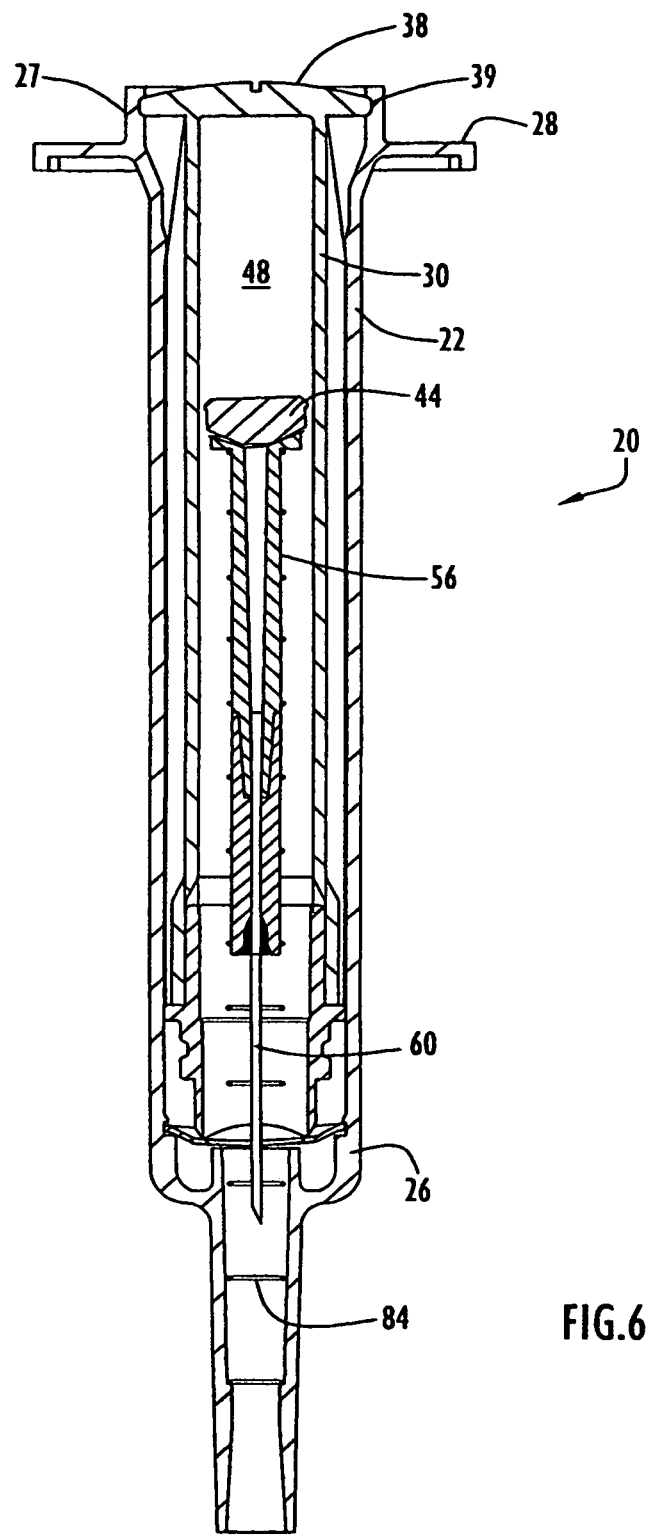
FIG. 6 is a side view in cross-section of the syringe of FIG. 1 with the needle fully retracted into the syringe after use.

The proximal end of plunger 30 includes a convex surface or domed thumb pad 38 and a radially extending flange 39 that facilitates engagement with the fingers and/or thumb of the user during operation of the syringe. Similarly, the main body portion 24 of the barrel includes a radially extending flange 28 disposed near its proximal end for facilitating engagement with the fingers and/or thumb of the user during operation. An extended barrel portion 27 extends between flange 28 and the proximal end of the barrel and is slightly greater in internal diameter in comparison to the remainder of main body portion 24. The extended barrel portion 27 is also of a sufficient longitudinal dimension, and is slightly smaller in internal diameter than the transverse dimension of the plunger defined at the flange 39, such that, when plunger 30 is fully depressed within the barrel, plunger flange 28 forces a slight flexure of the extended barrel portion 27 at the proximal end of the barrel to permit the flange to enter the extended barrel portion. Upon complete depression of the plunger within the barrel, the plunger flange 39 engages in a snap-tight locking relationship with an annular groove 29 disposed along the interior wall of the extended barrel portion near the proximal end of the barrel to prevent removal of the plunger from the barrel (as depicted in FIG. 6).

Figure 2:
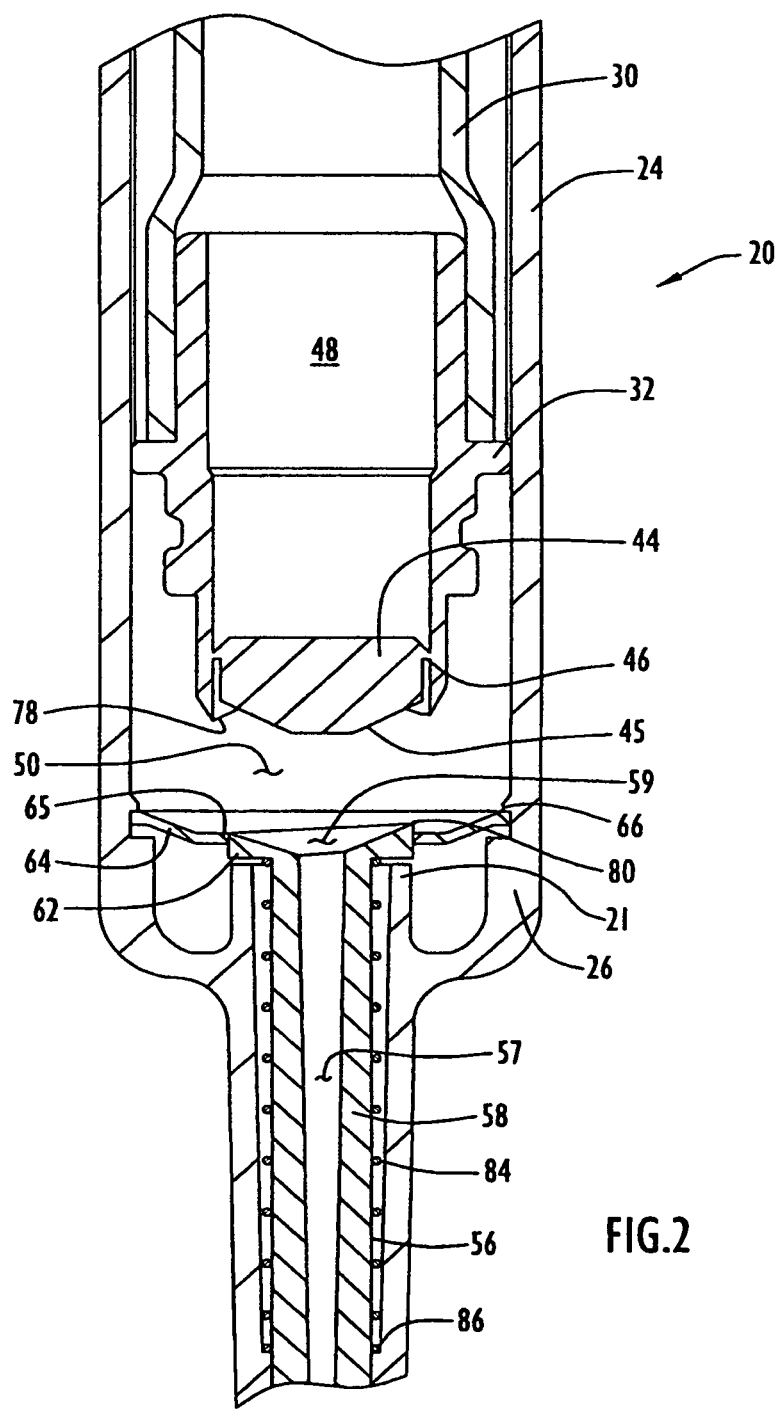
FIGS. 2-5 are partial side views in cross-section of the syringe of FIG. 1 detailing interaction of the distal end of the plunger and the proximal end of the needle assembly at varying stages of depression of the plunger to facilitate retraction of the needle assembly into the syringe in accordance with the present invention.
Figure 3:
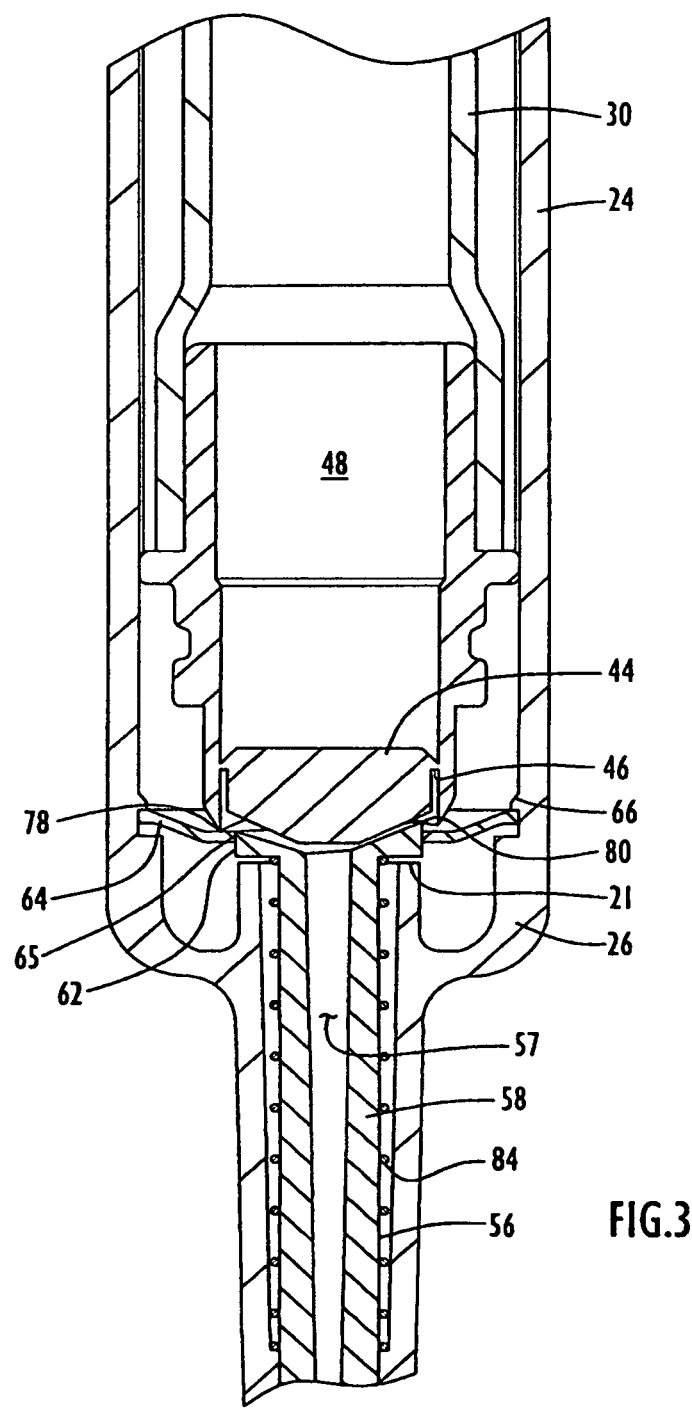

Referring to FIG. 2, the distal end of plunger 30 is sealingly closed by an end wall 44, where the end wall is preferably molded as a part of the plunger. The end wall 44 includes an annular notch or scored section 46 extending around a periphery of the end wall. The scored section 46 defines a thin membrane or reduced material section that is torn or broken away during depression of the plunger to facilitate access to a retraction cavity 48 of the plunger during use of the syringe as described below. The end wall 44 further includes a frusto-conical surface 45 that extends toward the distal end of the barrel and partially engages with a frusto-conical cavity portion 59 of the needle assembly 56 when the plunger is fully depressed into the barrel as described below. Alternatively, the end wall may be formed with any suitable outwardly or inwardly extending surface (e.g., conical, convex, V-shaped, multifaceted, etc.) or even a flat surface as desired for a particular application.

The needle assembly 56 includes a needle holder or stem 58 that connects with a syringe needle 60 and is affixed within the distal end extension 26 of the barrel such that the needle 60 extends from the distal end of the barrel prior to and during use (as depicted in FIG. 1). The needle stem 58 and needle 60 preferably releasably engage with each other (e.g., via a threaded engagement). An axially extending cavity 57 extends from a proximal end of the needle stem 58 to the connection point with the needle 60 in order to facilitate fluid communication between the needle and fluid cavity 50 within the barrel. In addition, cavity 57 includes a widened portion 59 at the proximal end of needle stem 58 that is frusto-conical in configuration and widens toward the proximal end of the barrel so as to generally correspond with the frusto-conical surface 45 of the plunger 30. Specifically, the widened portion 59 is slightly offset from alignment with the central axis of the needle stem 58 (e.g., by about 3-5°) and includes angled surfaces that are slightly different than the angled surfaces of the plunger end wall 44 such that, when the plunger is depressed toward the needle assembly, the frusto-conical plunger end wall surface 45 does not completely align and correspond with widened portion 59. The needle stem 58 further includes a radially extending flange 62 at its proximal end that is suitably dimensioned to engage with a step or ledge 21 disposed along an interior surface of the distal end extension 26 in order to prevent movement of the needle assembly distally beyond ledge 21 during depression of the plunger toward the distal end of the barrel.

A disc-shaped stem ring 64 is secured to and extends radially from the flange 62 of needle stem 58 to engage with the interior wall surface of distal end extension 26 of the barrel. The stem ring 64 is preferably molded as a part of flange 62 and needle stem 58 and includes a notch or scored section 65 at the connection point of stem ring 64 and needle stem 58. The scored section 65 defines a thin membrane or reduced material section that is torn or broken during operation of the syringe to facilitate retraction of needle assembly 56 in the manner described below. The stem ring 64 is preferably dimensioned to facilitate a partial sliding of a broken portion of the stem ring along the interior wall surface of the barrel when the plunger is depressed to engage with needle stem 58 as described below.

The diameter of the stem ring can be selected to be slightly smaller, the same, or slightly larger than the diameter of the interior wall surface of distal end extension 26 at the location where the stem ring engages the barrel. In the embodiment depicted in FIGS. 1-6, the diameter of stem ring 64 is slightly larger in comparison to the diameter of the interior wall surface of the barrel that engages with the stem ring such that the stem ring is slightly compressed during engagement with the barrel and forms an effective fluid tight seal. The dimensions of the stem ring are further selected to provide a compression fit/fluid tight seal at the stem ring/barrel interior wall interface while facilitating a sliding of the stem ring with the barrel interior wall surface when the plunger is completely depressed within the barrel.

A radial protrusion or shoulder 66 is disposed along the interior surface and near the proximal end of the distal end extension 26 of the barrel. The shoulder 66 engages with stem ring 64 to prevent movement of the needle assembly toward the proximal end of the barrel while the stem ring remains attached with needle stem 58. Alternatively, it is noted that a series of radially spaced protrusions can be provided to achieve the same result of engaging or locking the stem ring at the barrel distal end extension so as to prevent movement of the needle assembly toward the barrel proximal end while the stem ring is still attached to the needle stem. A resilient member 84 (e.g., a coil spring) is disposed between the flange 62 of needle stem 58 and an interior ledge 86 disposed on the interior surface of the distal end extension 26 at a location between the radial protrusion 64 and the distal end of the barrel. When the needle assembly 56 is press fit into the distal end extension 26 of the barrel (as described below) such that stem ring 64 is extended distally beyond the radial protrusion 66 of the barrel, resilient member 84 is compressed to bias the needle assembly toward the proximal end of the barrel.

The syringe 20 is designed so that complete depression of plunger 30 within barrel 22 facilitates a combined tearing or breaking away of end wall 44 of the plunger and also a tearing or breaking away of the stem ring 64 from flange 62 of needle stem 58 to facilitate retraction of the needle stem and the needle 60 into the retraction cavity 48. In particular, plunger 30 includes an annular edge 78 at its distal end that is inclined at a slight angle (e.g., about 3-5°) to a plane that is perpendicular to the central axis of the syringe. Similarly, the needle stem 58 includes an annular edge 80 at its proximal end that is inclined at a slight angle (e.g., about 3-5°) to a plane that is perpendicular to the central axis of the syringe.

The plunger and the needle stem can be assembled within the syringe such that the apexes formed by their facing annular surfaces 78 and 80 are aligned at any selected orientation with each respect to each other. The specific orientation of the apexes of the plunger and needle stem with respect to each other within the syringe is not of particular importance to the function of the syringe. Thus, while FIGS. 1-5 depict the apexes of annular surfaces 78 and 80 of the plunger and needle stem as being offset from each other by a rotational angle of about 180°, the apexes could also be substantially aligned with each other or offset by any other selected rotational angle (e.g., 45°, 90°, etc.) without affecting the operability of the retraction feature of the syringe. The annular surfaces 78 and 80 of the plunger and needle stem are further suitably dimensioned in the longitudinal direction of the syringe to facilitate engagement with the plunger end wall 44 and stem ring 64 at and/or near their scored sections 46 and 65 upon complete depression of the plunger, which in turn facilitates a tearing or breakage of end wall 44 from the plunger and a tearing or breakage of stem ring 64 from needle stem flange 58 to initiate retraction of needle assembly 56 into retraction cavity 48 of the plunger. Alternatively, the annular surface 78 of the plunger can be oriented to engage with a portion of the needle stem that is removed from the scored section 65 a suitable distance (e.g., closer to the outer diameter of the stem ring and interior wall surface of the barrel) to establish a desired degree of leverage for the plunger with respect to the scored section 65 as the plunger engages the needle stem and thus facilitate easier and more efficient tearing or breakage of the stem ring from the needle stem flange during operation of the syringe.

Assembly of the syringe is achieved by first inserting the resilient member 84 and then needle assembly 56 (with or without the needle 60) into opening 23 at the proximal end of barrel 22, through main body portion 24 and into the distal end extension 26. As the stem ring 64 of needle stem 58 encounters annular shoulder 66 of the barrel, the stem ring is compressed slightly and forced distally beyond the shoulder 66 in a snap-fit engagement. Once stem ring 64 is forced distally beyond shoulder 66, the needle assembly 56 is locked in place within the distal end extension 26, and resilient member 84 is compressed to bias the needle assembly proximally within the syringe. The stem ring 64 remains compressed to a selected degree between flange 62 and the barrel interior wall surface in this locked configuration and provides an effective fluid tight seal at its compressed fit contact point with the barrel. The plunger 30 is then inserted into opening 23 of barrel 22 and axially displaced a suitable distance to facilitate use of the syringe. The needle 60 may be connected with needle stem 58 prior to insertion of the needle assembly into barrel 22. Alternatively, needle 60 may be connected with the connecting portion of needle stem 58 after securing the needle stem within the barrel. In either case, needle 60 protrudes from the opening at the distal end of the barrel after assembly to facilitate use of the syringe.

In operation, the distal end of the plunger is displaced a suitable distance toward the proximal end of the barrel to draw fluid from needle 60 into fluid cavity 50. Upon injection of the needle into an injection site, the plunger is then depressed toward the distal end of the barrel to force fluid from cavity 50 and through needle 60. Referring to FIGS. 2-5, as the plunger is further depressed within the barrel, the frusto-conical surface 45 of plunger end wall 44 moves into the widened portion 59 of central cavity 57 of needle stem 58 to force any remaining fluid through the needle prior to retraction (thus reducing "dead" space between the engaging portions of the plunger and needle assembly). In addition, the apex of annular edge 80 of needle stem 58 engages a portion of end wall 44 at or near frusto-conical surface 45 to initiate a tearing or breaking away of end wall 44 from plunger 30. Approximately contemporaneously, the apex of annular edge 78 of the plunger engages a portion of stem ring 64 at or near its scored section 65, forcing a tearing or breaking away of the stem ring from flange 62 along scored section 65 at the point of contact between the stem ring and the plunger.

Figure 4:
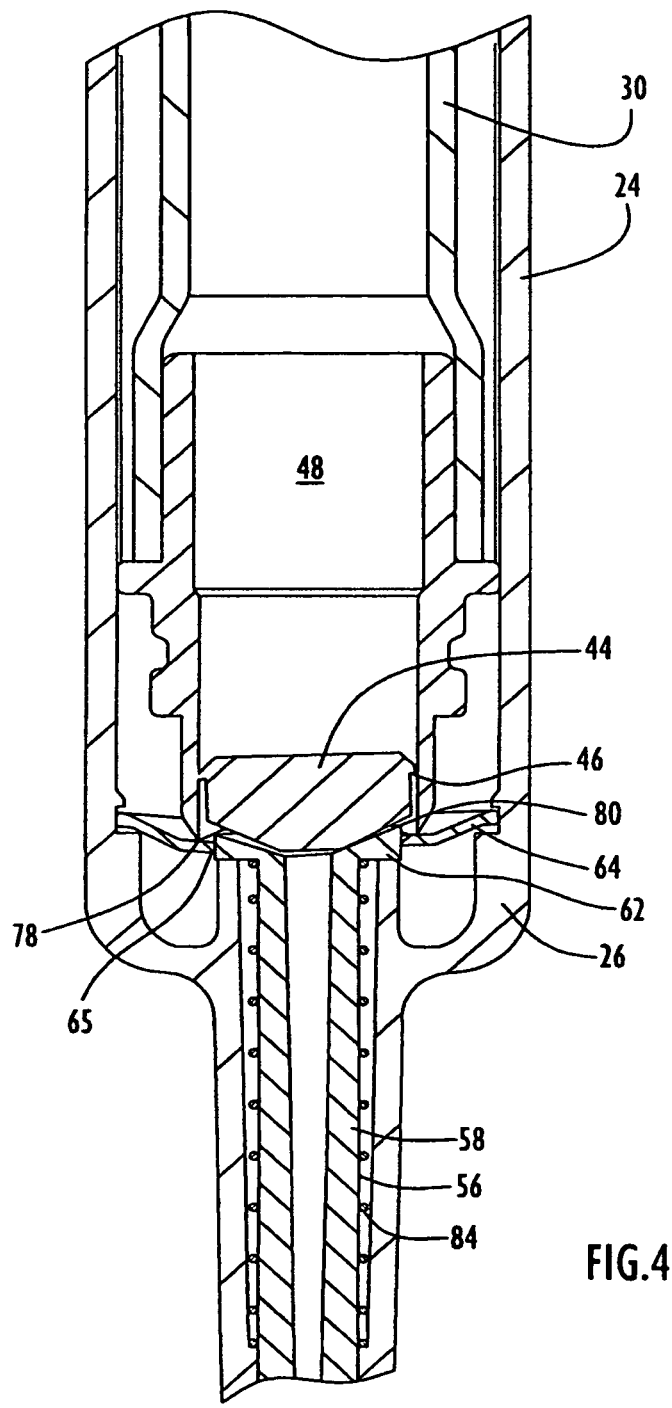
Figure 5:
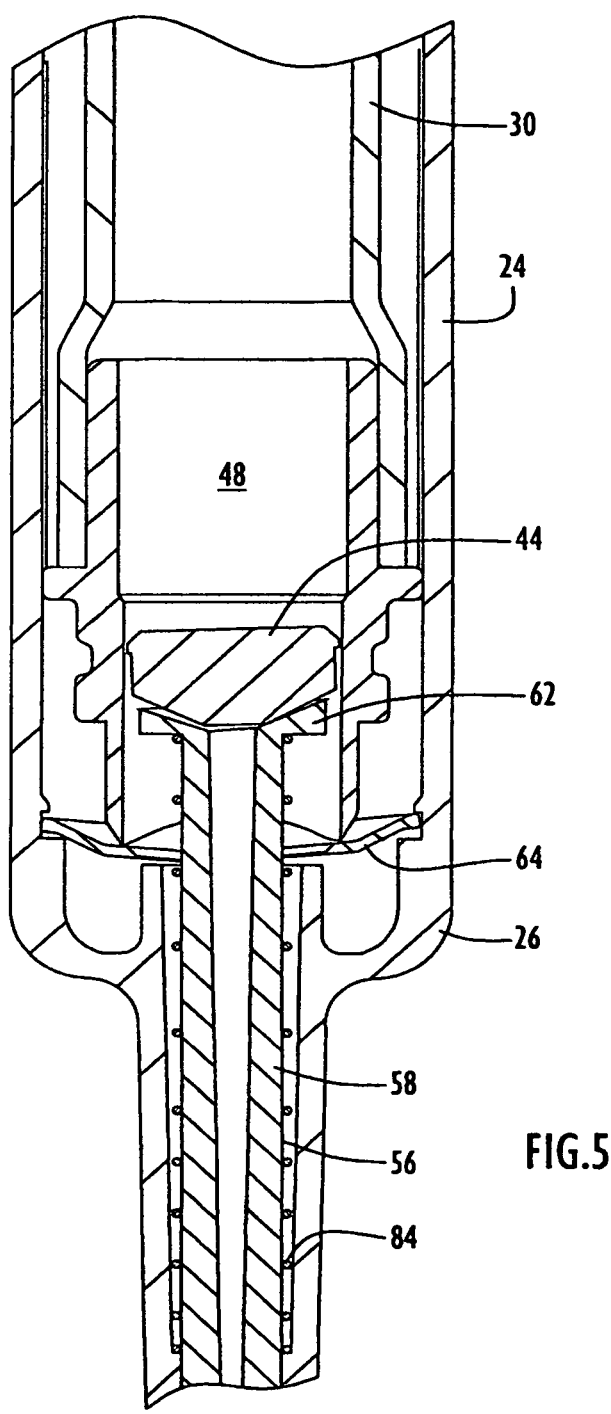

Complete depression of the plunger within the barrel further forces plunger annular edge 78 against stem ring 64, causing the portion of the stem ring that has already broken away from flange 62 to slide distally a short distance along the interior wall of the barrel so as to become oriented at a slight angle with respect to the central axis of needle stem 58 (see FIG. 4). In addition, the portion of the stem ring that has not broken away is prevented from moving distally until it has become broken away from the needle stem. This sliding of the broken portion of the stem ring 64 along the interior wall of the barrel, in combination with the continued pressure applied by the fully depressed plunger to the stem ring, results in a progressive tearing or breakage of the stem ring in both directions along scored section 65 until the stem ring is fully separated from tab 62. In addition, the forced engagement of annular edge 80 of needle stem 58 with plunger end wall 44 results in a progressive tearing or breakage of the end wall in both directions along scored section 46, resulting in complete separation of the end wall from plunger 30. It is noted that breaking the end wall from the plunger and also the stem ring from the tab of the needle stem requires no cutting action by annular edges 78 and 80 of the plunger and needle stem. In fact, it is not necessary for annular edges 78 and 80 to make any contact with scored sections 65 and 46 to achieve the tearing or breakage, since the opposing forces applied by the engaging end surfaces of the plunger and the needle stem are sufficient to achieve complete breakage of plunger end wall 44 from the plunger and stem ring 64 from the needle stem.

The design of the syringe is configured such that end wall 44 is completely separated from plunger 30 immediately prior to or substantially simultaneously with the complete separation of stem ring 64 from tab 62. Alternatively, the syringe can also be configured such that complete separation of the stem ring from the tab of the needle stem occurs immediately prior to complete separation of the end wall from the plunger, such that the proximal bias of the needle assembly assists in forcing complete tearing of the plunger end wall. Once complete separation of the stem ring from the tab of the needle stem and complete separation of the end wall from the plunger is achieved, resilient member 84 forces needle stem 58 and needle 60, along with end wall 44, proximally into the retraction cavity 48 within the plunger (see FIGS. 5 and 6).

As can be seen from FIG. 6, when plunger 30 has been fully depressed within barrel 22 and retraction of needle assembly 56 has occurred, flange 39 of the plunger extends slightly into the extended barrel portion 27 and is locked within annular groove 29. In this locked position, removal of the plunger from the barrel is prevented.

Figure 7:
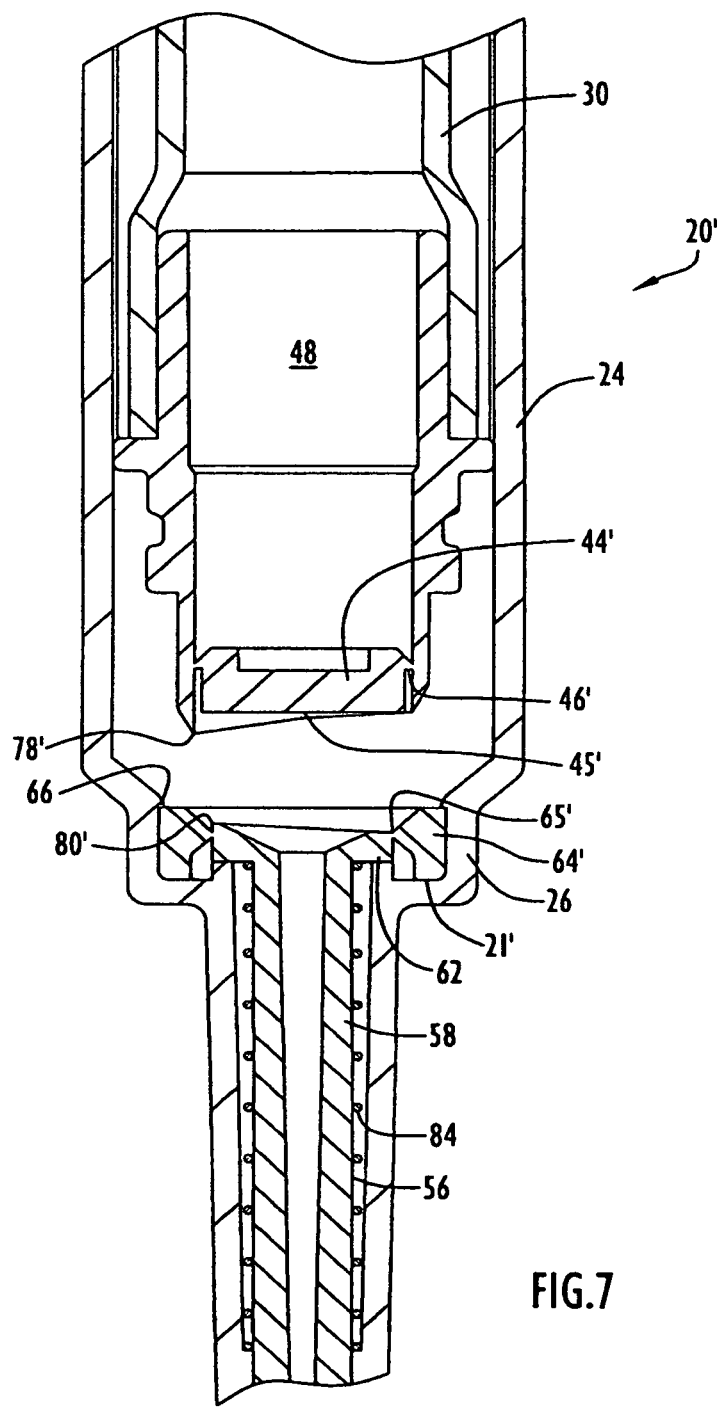
FIGS. 7-10 are partial side views in cross-section of an alternative embodiment of a syringe in accordance with the present invention, where the figures detail interaction of the distal end of the plunger and the proximal end of the needle assembly at varying stages of depression of the plunger to facilitate retraction of the needle assembly into the syringe.
Figure 8:
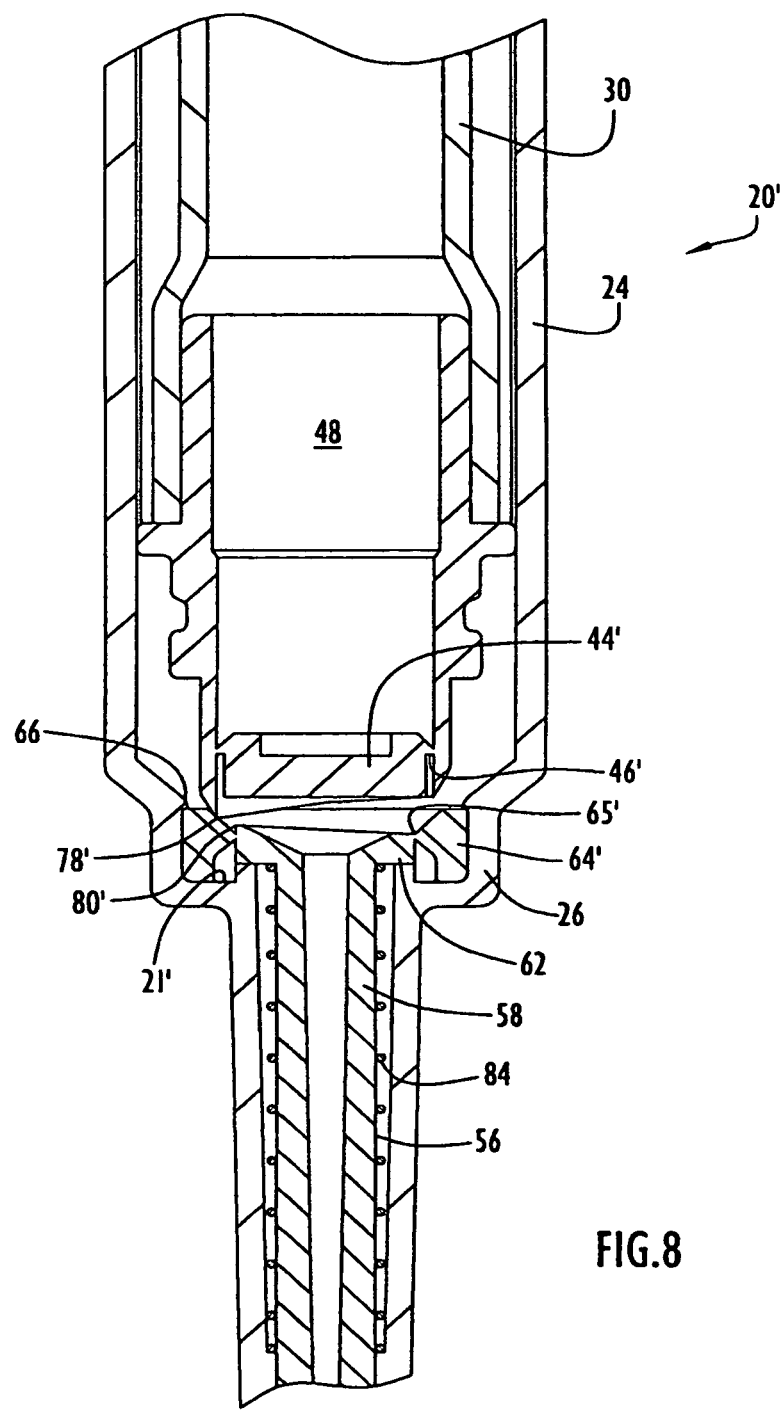
Figure 9:
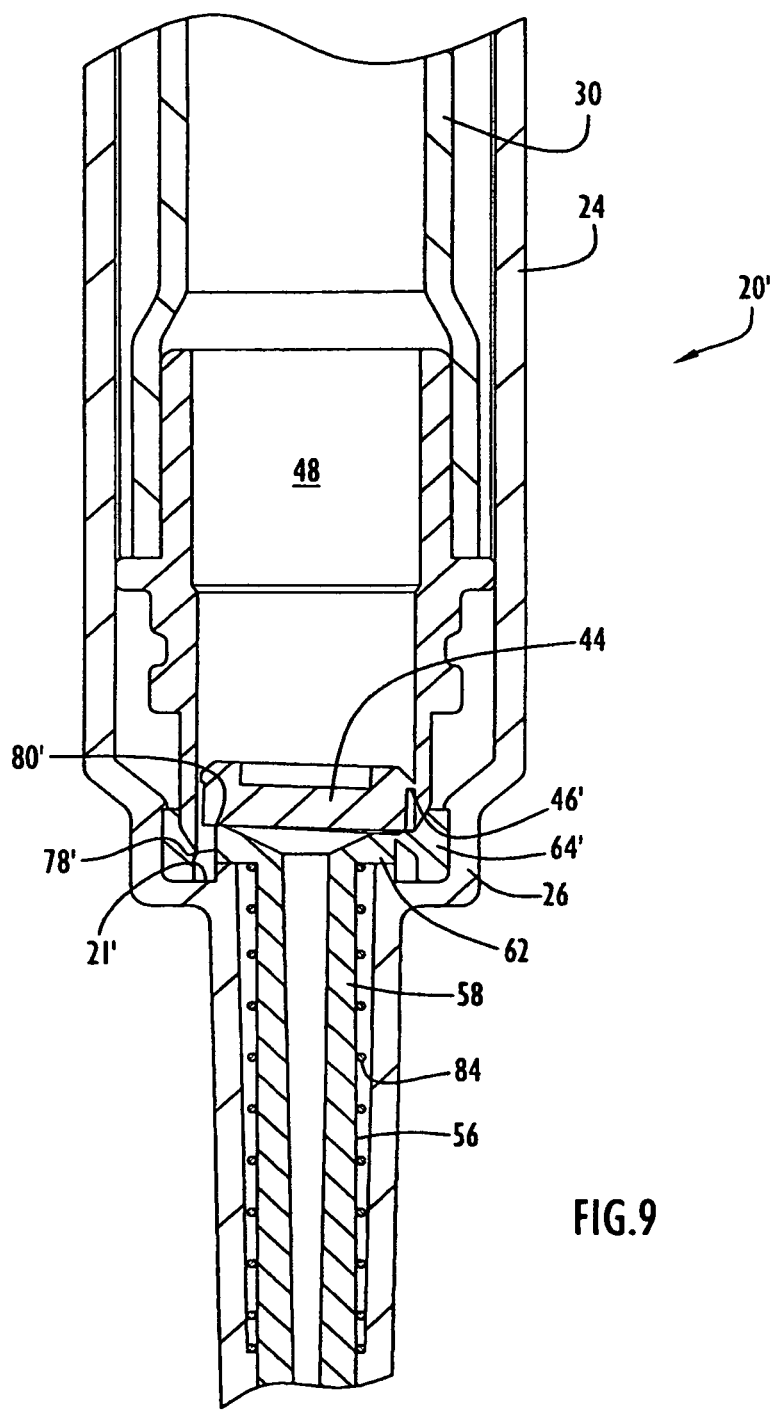
Figure 10:
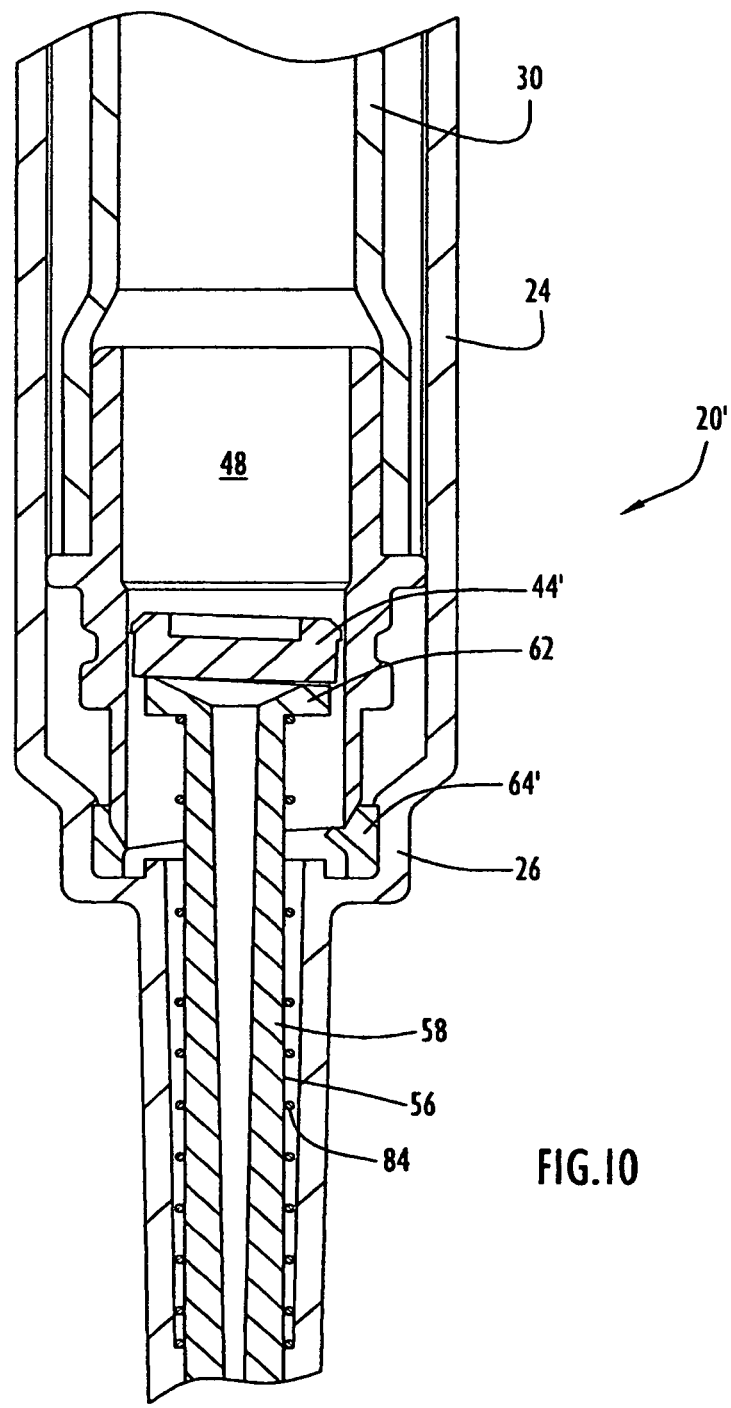

An alternative embodiment of a syringe is depicted in FIGS. 7-10 and described below. The syringe is similar in design, assembly and operability to the syringe described above and depicted in FIGS. 1-6, with the same numerals designating similar components. The main differences between the syringe of FIGS. 1-6 and the syringe of FIGS. 7-10 are the design of the plunger end wall, the stem ring for the needle assembly, and the locking ledges/protrusions along the barrel interior wall surface that function to lock the needle assembly in a fixed manner prior to retraction. Referring to FIG. 7, needle stem 58 of the syringe 20' includes a radially extending flange 62 and a stem ring 64' that is attached to the flange 62 (preferably, the stem ring is molded as a part of the flange) and extends radially therefrom so as to engage with the interior wall of the barrel 22 to provide an effective fluid tight seal at the engagement. The stem ring 64' of the embodiment of FIG. 7 has a thickness dimension that is slightly greater than the stem ring 64 of the previous embodiment (depicted in FIGS. 1-6) and includes a distally extending portion that fits within and engages an annular shoulder or seat 21' defined along the interior wall of the barrel. The stem ring 64' is further suitably dimensioned such that, when the needle stem 58 is inserted within the barrel and forced distally beyond annular shoulder 66 within the barrel, stem ring 64' fits snugly between the annular shoulder 66 and the seat 21' to substantially prevent any proximal or distal movement of the needle stem within the barrel prior to retraction of the needle assembly. The stem ring 64' further includes an annular notch or scored section 65' at the connection point of the stem ring 64' and needle stem 58 defining a thin membrane or reduced material section that is torn or broken away during retraction of the syringe.

The end wall 44' secured at the distal end of plunger 30 (where the end wall is preferably molded as a part of the plunger) includes an annular notch or scored section 46' extending around a periphery of the end wall defining a thin membrane or reduced material section that is torn or broken away, during depression of the plunger. The end wall surface 45' that faces the needle assembly is substantially flat, as opposed to the frusto-conical surface 45 of the embodiment depicted in FIGS. 1-6. Similarly to that previous embodiment, the facing annular surfaces 78' and 80' of the plunger 30 and needle stem 58 are both inclined at a slight angle (e.g., about 3-5°) to a plane that is perpendicular to the central axis of the syringe so as to define an apex at each annular surface that facilitates the application of pressure to both the plunger end wall 44' and the stem ring 64' during depression of the plunger within the barrel.

Operation of the syringe 20' is now described with reference to FIGS. 7-10. Use of the syringe is initiated by displacing the distal end of the plunger a suitable distance toward the proximal end of the barrel to draw fluid from the needle into fluid cavity 50. Upon injection of the needle into an injection site, the plunger is then depressed toward the distal end of the barrel to force fluid from cavity 50 and through the needle. As the plunger is further depressed within the barrel, the apex of annular edge 80' of needle stem 58 engages a portion of end wall 44' at or near end wall surface 45' to initiate a tearing or breaking away of end wall 44' from plunger 30.

Approximately contemporaneously, the apex of annular edge 78' of the plunger engages a portion of stem ring 64' at or near its scored section 65', forcing a tearing or breaking away of the stem ring from flange 62 along scored section 65' at the point of contact between the stem ring and the plunger. However, unlike in the previous embodiment, the free portion of the stem ring 64' that has already broken away from flange 62 does not slide along the interior wall of the barrel. Rather, this free portion of stem ring 64' is substantially prevented from moving distally within the barrel due to seat 21' which buts against the stem ring.

Complete depression of the plunger within the barrel forces further progressive tearing or breaking away of both stem ring 64' in both directions along its scored section 65' from flange 62 and the end wall 44' in both directions along its scored section 46' from the plunger 30. As in the previous embodiment, syringe 20' is preferably designed such that end wall 44' is completely separated from plunger 30 immediately prior to or substantially simultaneously with the complete separation of stem ring 64' from tab 62. Alternatively, the syringe can also be configured such that complete separation of the stem ring from the tab of the needle stem occurs immediately prior to complete separation of the end wall from the plunger, such that the proximal bias of the needle assembly assists in forcing a complete rupture of the plunger end wall. Once complete separation of the stem ring from the tab of the needle stem and complete separation of the end wall from the plunger is achieved, resilient member 84 forces needle stem 58 and needle, along with end wall 44', proximally into the retraction cavity 48 within the plunger. Thus, the manner in which retraction of the needle assembly is initiated, like in the previous embodiment, requires no cutting action by annular edges 78' and 80' of the plunger and needle stem.

Figure 11:
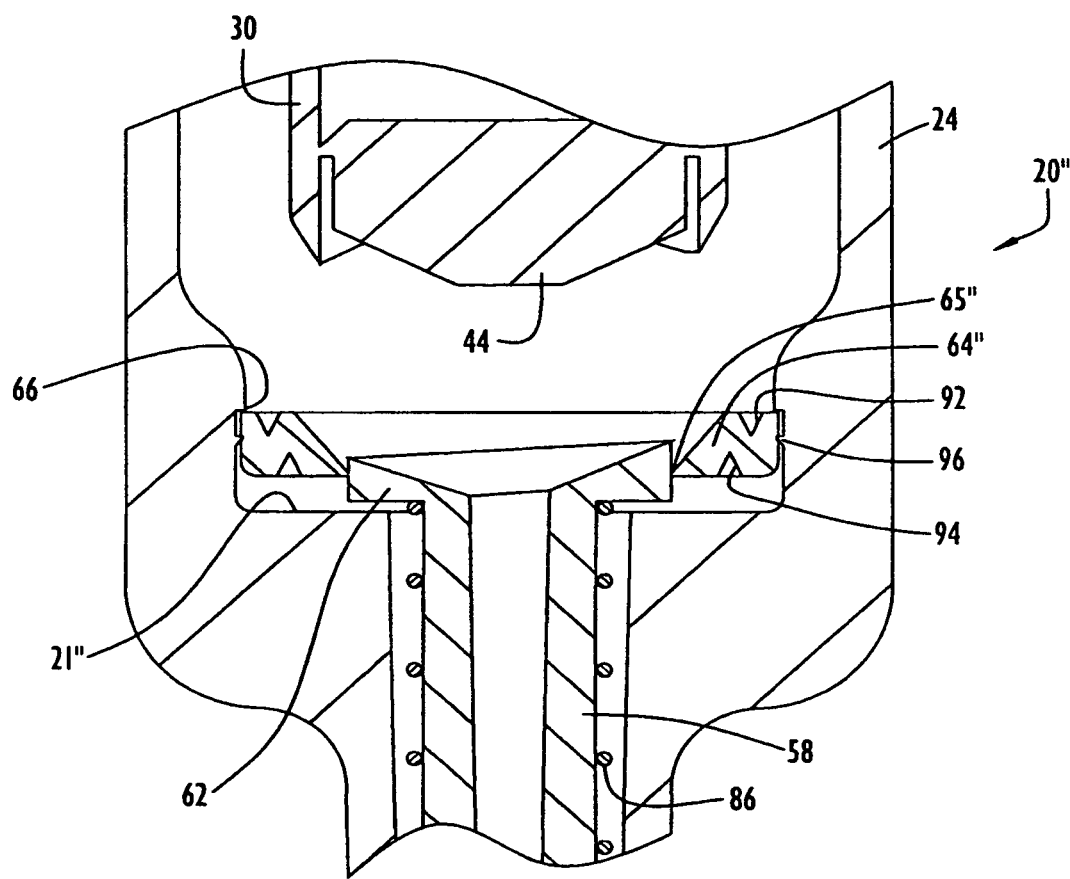
FIG. 11 is a partial side view in cross-section of another alternative embodiment of a syringe in accordance with the present invention.

A further embodiment of a syringe is depicted in FIG. 11 and described below. The syringe is similar in design, assembly and operability to the syringe described above and depicted in FIGS. 1-6, with the same numerals designating similar components. However, the stem ring of the syringe of FIG. 11 is slightly modified to include one or more additional notches radially spaced from the notched or scored section along one or more surfaces of the stem ring. The additional notches enhance the tearing or breaking of the stem ring from the needle stem along the scored section. It is noted that any suitable number of notches (e.g., one or more) can be disposed at any suitable locations along any one or more surfaces of the stem ring. The notches may further extend in a radial manner with respect to the center of the stem ring for any selected radial length (e.g., 45°, 90°, 180°, 360°, etc.).

Referring to FIG. 11, the stem ring 64" includes scored section 65" near the connection point with flange 62 of needle stem 58 and a pair of notched sections 92 and 94 that are disposed on opposing surfaces of stem ring 64" and at radially spaced locations between scored section 65" and the periphery of the stem ring. The stem ring further includes a groove extending along its outer peripheral surface that engages with a notch 94 disposed along the interior surface of main body portion 24 of the barrel between annular shoulder 66 and ledge 21".

Assembly of syringe 20" is substantially similar to assembly of the syringes described above, with the additional feature of stem ring 64" being pushed into position within the barrel such that the peripheral groove of the stem ring mates with barrel protrusion 96. When the distal end of the plunger engages stem ring 64" to begin tearing or breakage of the stem ring from needle stem 58 at scored section 65", the stem ring is substantially prevented from sliding toward ledge 21" due to the engagement of the stem ring at its peripherally located groove and barrel protrusion 96. In addition, notched sections 92 and 94 enhance the flexibility of the stem ring as it is contacted by the plunger to further enhance breakage of the stem ring at its scored section 65".

The syringes described above and depicted in the figures can be modified in any number of ways without falling outside of the scope of the present invention. For example, the stem ring for the needle stem can be affixed to the interior surface of the barrel wall in any suitable manner (e.g., by thermal or ultrasonic bonding, adhesion, etc.) rather than being held in a frictional/compression tight fit with the barrel wall. In such an embodiment, the portion of the stem ring that attaches to the interior barrel wall would not be forced to an angle with respect to the central axis of the syringe during separation of the stem ring from the needle stem. However, separation would still be induced along the scored section of the stem ring to facilitate a breakage of the stem ring from the needle stem.

Figure 12:
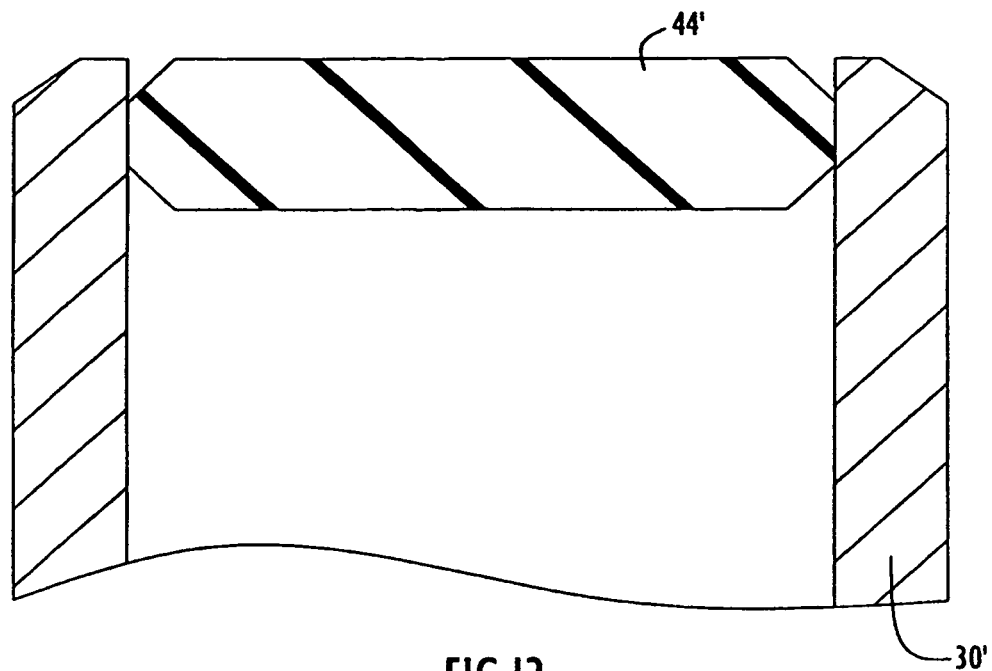
FIGS. 12 and 13 are partial views in cross-section of plungers for alternative syringe embodiments in accordance with the present invention.
Figure 13:
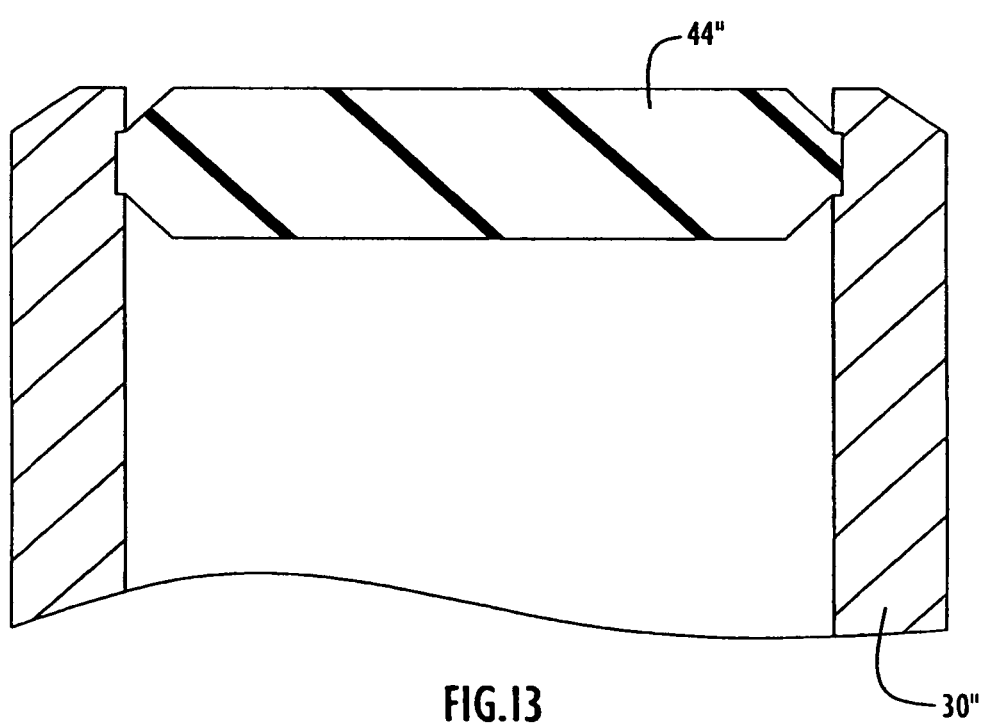

In other exemplary embodiments, the plunger end wall can be a plug or membrane that is frictionally fit to engage with interior surface portions within the hollow plunger or, alternatively, snap fit into one or more grooves within interior surface portions of the hollow plunger. For example, referring to FIG. 12, a hollow plunger 30' includes a plug 44' that frictionally engages an interior wall surface and is held within the plunger at the plunger distal end. In another embodiment depicted in FIG. 13, a hollow plunger 30" includes a plug 44" that is snap fit into a corresponding annular groove disposed along interior wall surface near a distal end of the plunger. In each of these embodiments, the plunger membrane or plug is of suitable dimensions and is held in place with respect to the plunger during movement of the plunger within the barrel. Upon engagement of the plunger plug with portions of the needle stem, the plunger plug is forced from such engagement with the plunger and retracts with the needle stem and needle into the retraction cavity of the plunger.

Other features can also be provided between the stem ring or needle holder and the barrel to prevent rotation of the stem ring and needle holder within the barrel after assembly of the syringe (e.g., when a needle hub is attached to the needle holder via a threaded engagement, the stem ring and needle holder will resist rotational movement). For example, the stem ring/needle holder can be provided with grooves, notched protrusions and/or teeth that engage with complimentary grooves, notches and/or teeth within the barrel when the needle holder is assembled within the barrel. This engagement between the needle holder and the barrel prevents rotational movement of the needle holder within the barrel, e.g., when a needle is connected (via a threaded engagement) with the needle holder. Alternatively, or in addition to the teeth and grooves, any other suitable complimentary engaging structure may also be provided between the needle holder and the barrel to minimize or substantially prevent any rotation of the needle holder with respect to the barrel when the syringe is completely assembled.

Other modifications to the syringe include providing cut-away sections in the extended portion at the proximal end of the barrel, where the cut-away sections provide access to gripping surfaces of the plunger thumb pad and flange for the user during aspiration of fluid into the fluid cavity of the syringe (i.e., when a portion of the plunger is pulled from the barrel). For example, two or more diametrically opposed cut-away sections can be provided along the extended barrel section. However, any suitable number of cut-away sections (e.g., one or more) can be provided in any suitable arrangement along the extended barrel section as desired for a particular application. The remaining sections of the extended barrel section will include a locking groove that engages with the thumb pad of the plunger to lock the plunger within the barrel in a similar manner as described above after use of the syringe.

Figure 14:
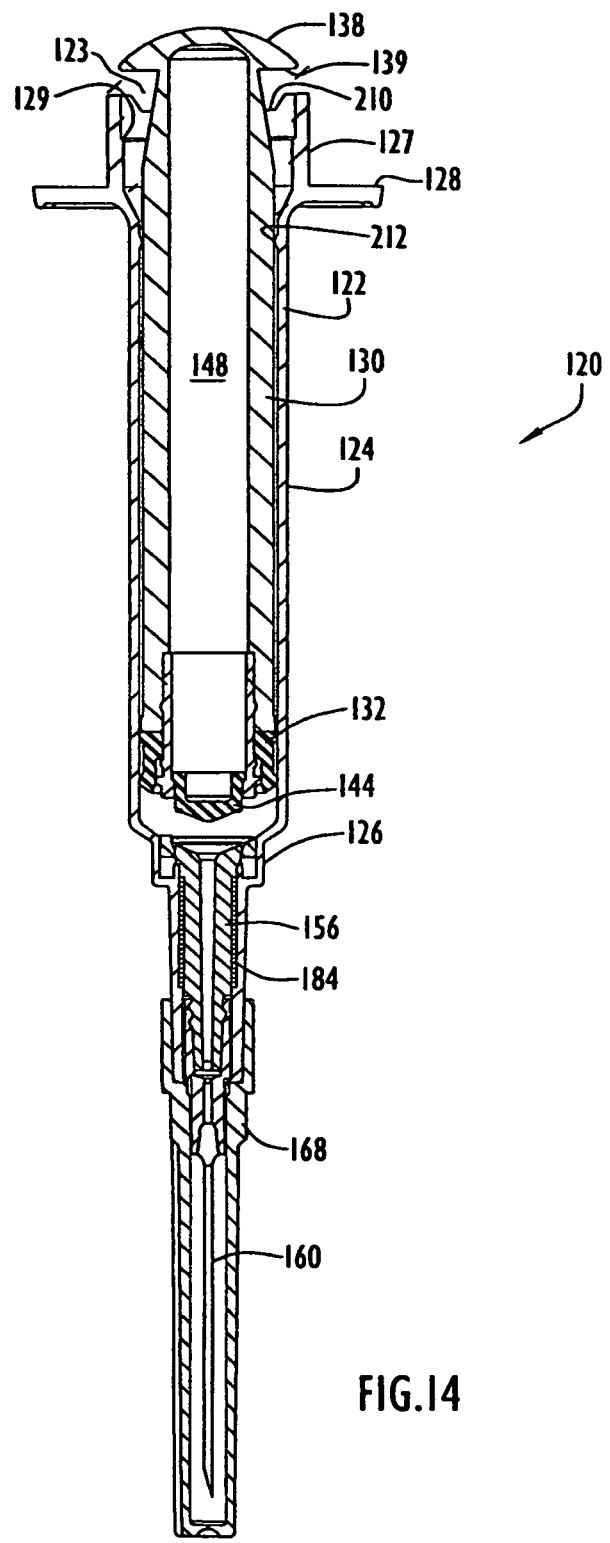
FIG. 14 is a side view in cross-section of a syringe in accordance with a further embodiment of the present invention, where the needle extends from the syringe barrel and the syringe is ready for use.

A syringe embodiment that incorporates some of the features as noted above, as well as further additional features, is depicted in FIGS. 14-21. The syringe is similar in design, assembly and operability to the syringes described above and depicted in FIGS. 1-6, with the additional features described below. Referring to FIG. 14, a medical syringe 120 includes a hollow cylindrical barrel 122 with an opening 123 at its proximal end and suitably dimensioned to receive a hollow plunger 130. The barrel further includes an opening at its distal end to permit exposure of a needle 160 from the syringe. The barrel 122 includes a main body portion 124 that receives and retains a portion of the plunger 130 and a distal end extension 126 of reduced internal diameter in relation to the main body portion 124 that receives a needle assembly 156 as described below. At least one bump or ridge 212 is disposed along an interior surface wall portion of the main body portion 124 within and near the proximal end of the barrel to resist or prevent complete removal of the plunger from the barrel during operation of the syringe. For example, the ridge could be continuous (e.g., forming a protruding annular ring) within the barrel. Alternatively, a series (e.g., two or more) of ridges can be provided at radially spaced locations along the interior barrel surface.

The plunger 130 includes a resilient seal 132 encircling the plunger near its distal end. A fluid cavity 150 is defined within the barrel 122 between the resilient seal 132 and other distal end portions of the plunger and a distal end 125 of the barrel main body portion 124, where the fluid cavity varies in volume based upon axial displacements of the plunger with respect to the barrel. A sheath 168 is removably secured to the distal end of the barrel 122 to enclose needle 160 secured within the barrel prior to use of the syringe. As in the previous embodiments, the barrel, plunger, resilient seal, sheath and all other components of the syringe may be constructed of any suitable medical grade materials (e.g., plastics and/or stainless steels) that facilitate operability of the syringe as described below. Further, the syringe can be designed with a suitable fluid cavity to meet any fluid volume capacity for a particular application (e.g., 1 cubic centimeter or cc, 3 cc, 5 cc, etc.).

The proximal end of plunger 130 includes a convex surface or domed thumb pad 138 and a radially extending flange 139 that facilitates engagement with the fingers and/or thumb of the user during operation of the syringe. Similarly, the main body portion 124 of the barrel includes a radially extending flange 128 disposed near its proximal end for facilitating engagement with the fingers and/or thumb of the user during operation. An extended barrel portion 127 extends between flange 128 and the proximal end of the barrel and is slightly greater in internal diameter in comparison to the remainder of main body portion 124. The extended barrel portion 127 is also of a sufficient longitudinal dimension, and is slightly smaller in internal diameter than the transverse dimension of the plunger defined at the flange 139, such that, when plunger 130 is fully depressed within the barrel, plunger flange 128 forces a slight flexure of the extended barrel portion 127 at the proximal end of the barrel to permit the flange to enter the extended barrel portion.

Figure 15:
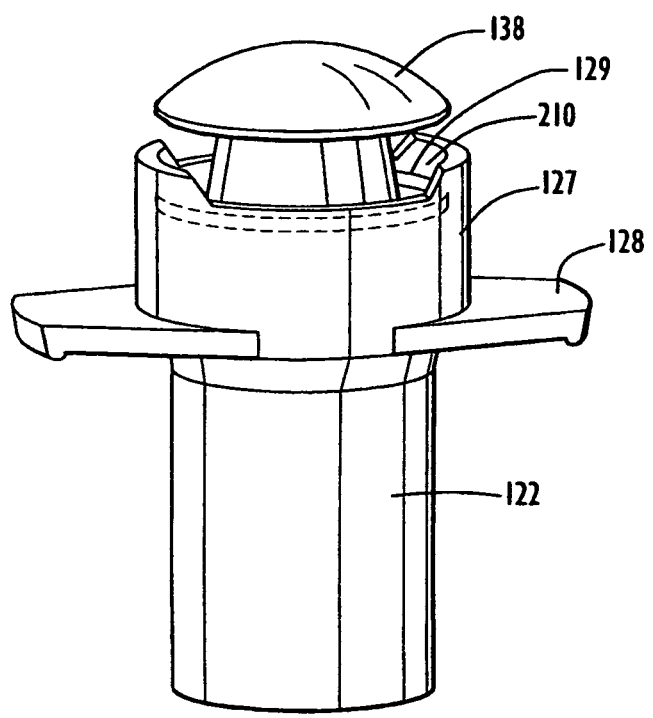
FIG. 15 is a partial view in perspective and partial section of the syringe of FIG. 14 including a proximal end portion of the syringe barrel.

Referring to FIG. 15, two diametrically opposed sections are removed from extended barrel portion 127, so as to form cut-out areas or portions 210 along the extended barrel periphery. The cut-out portions 210 facilitate exposure of sufficient portions of the plunger thumb pad 138 and flange 139 to assist the user of the syringe in gripping the plunger when the plunger is pulled from the barrel to initiate aspiration of fluid within the fluid cavity of the barrel as described below. While two cut-out sections are depicted, it is noted that any suitable number of cut-out sections can be provided (e.g., one or more) at any one or more selected locations along the extended barrel portion. Preferably, the extended barrel portion wall thickness and/or plastic or other materials from which this portion is formed are selected to facilitate a slight elastic and reversible deformation of the extended barrel portion when grasped by a user so as to further assist in axially displacing a portion of the plunger from the barrel during aspiration of fluid into the barrel.

An annular groove 129 is disposed along remaining interior wall sections (i.e., the wall sections that are separated by the cut-out sections) of the extended barrel portion near the proximal end of the barrel. Upon complete depression of the plunger within the barrel and retraction of the syringe within the plunger, the plunger flange 139 engages in a snap-tight locking relationship with annular groove 129 to prevent removal of the plunger from the barrel.

Figure 17:
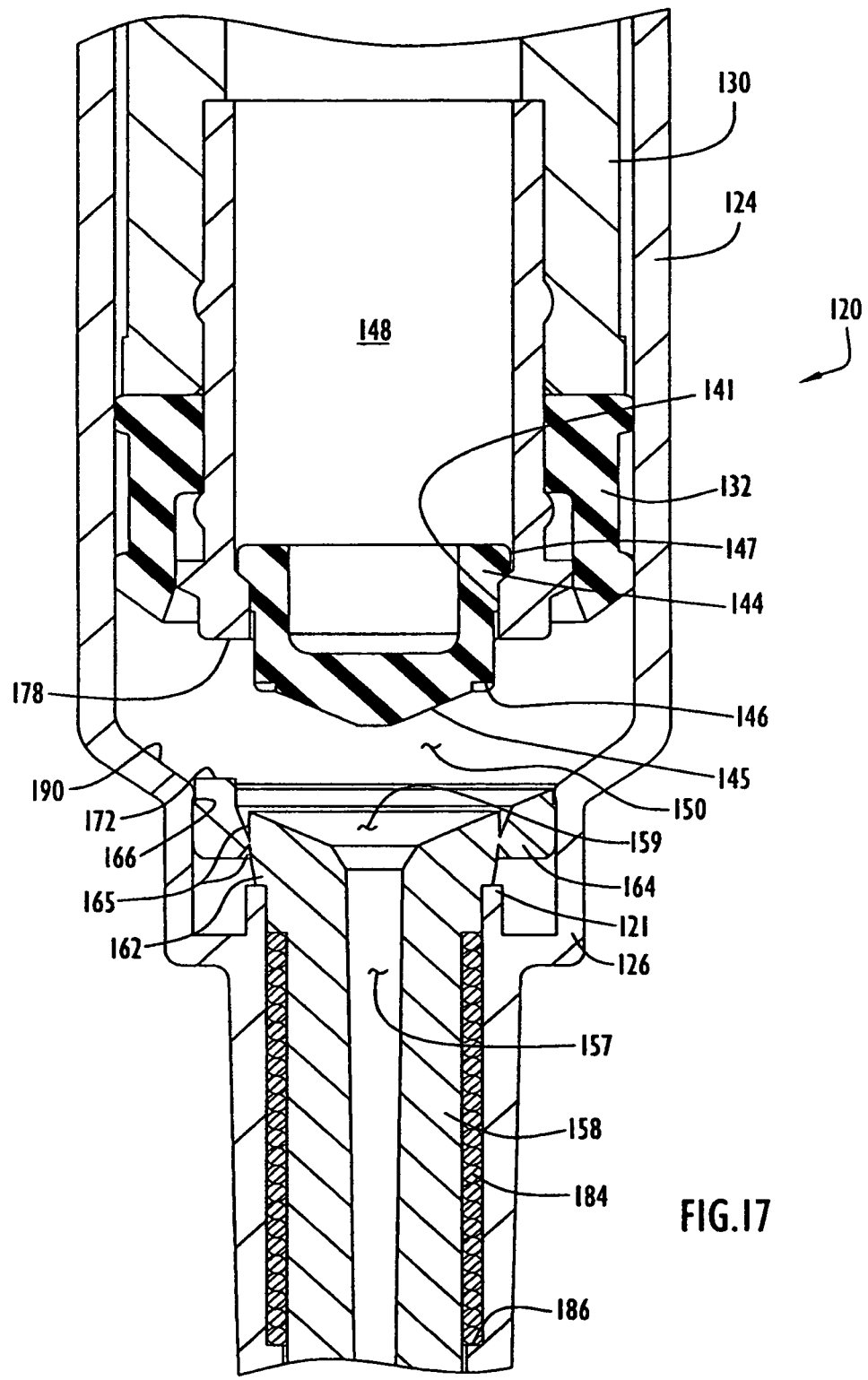
FIGS. 17-20 are partial side views in cross-section of the syringe of FIG. 14 detailing interaction of the distal end of the plunger and the proximal end of the needle assembly at varying stages of depression of the plunger to facilitate retraction of the needle assembly into the syringe in accordance with the present invention.
Figure 18:
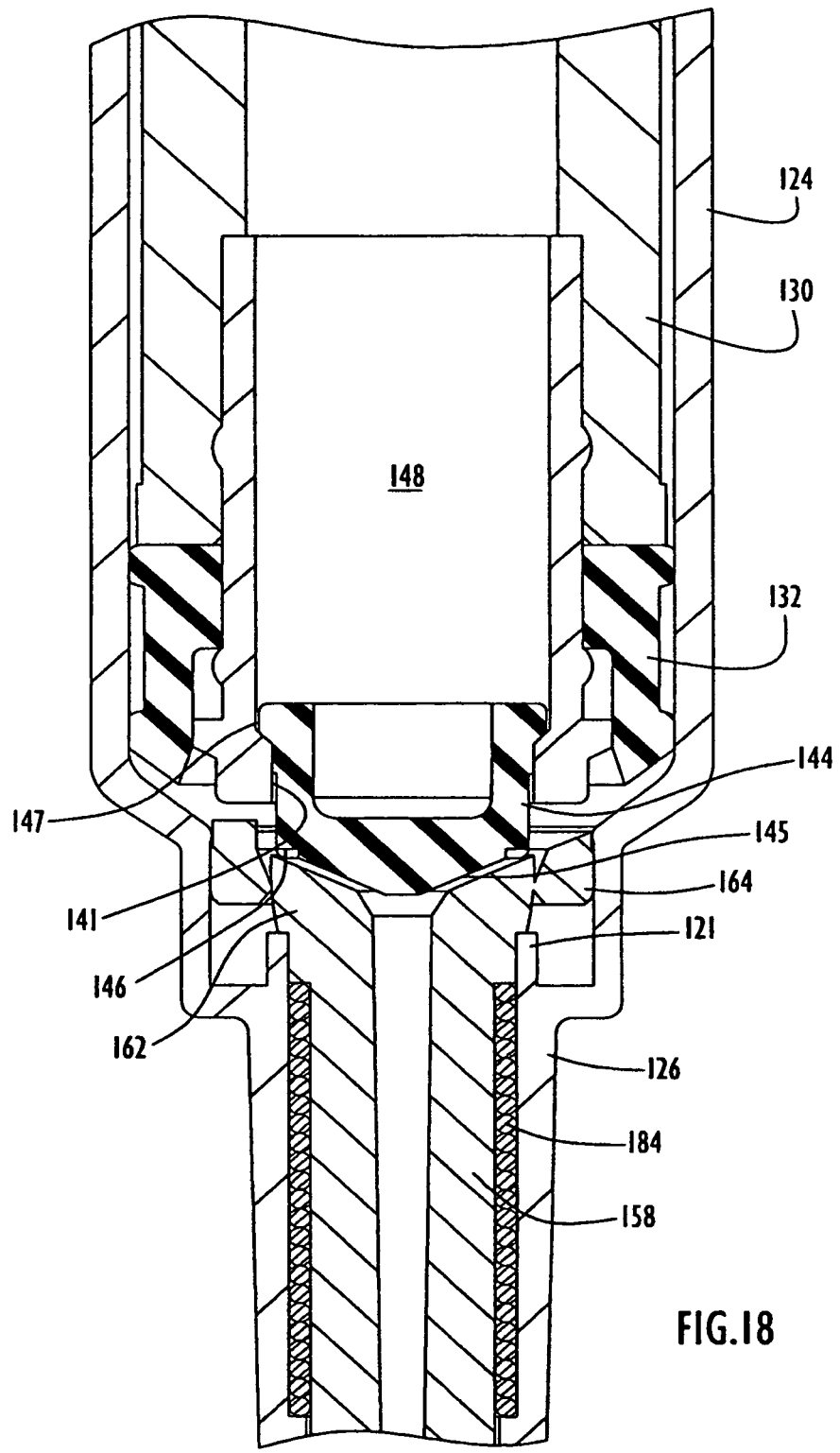
Figure 19:
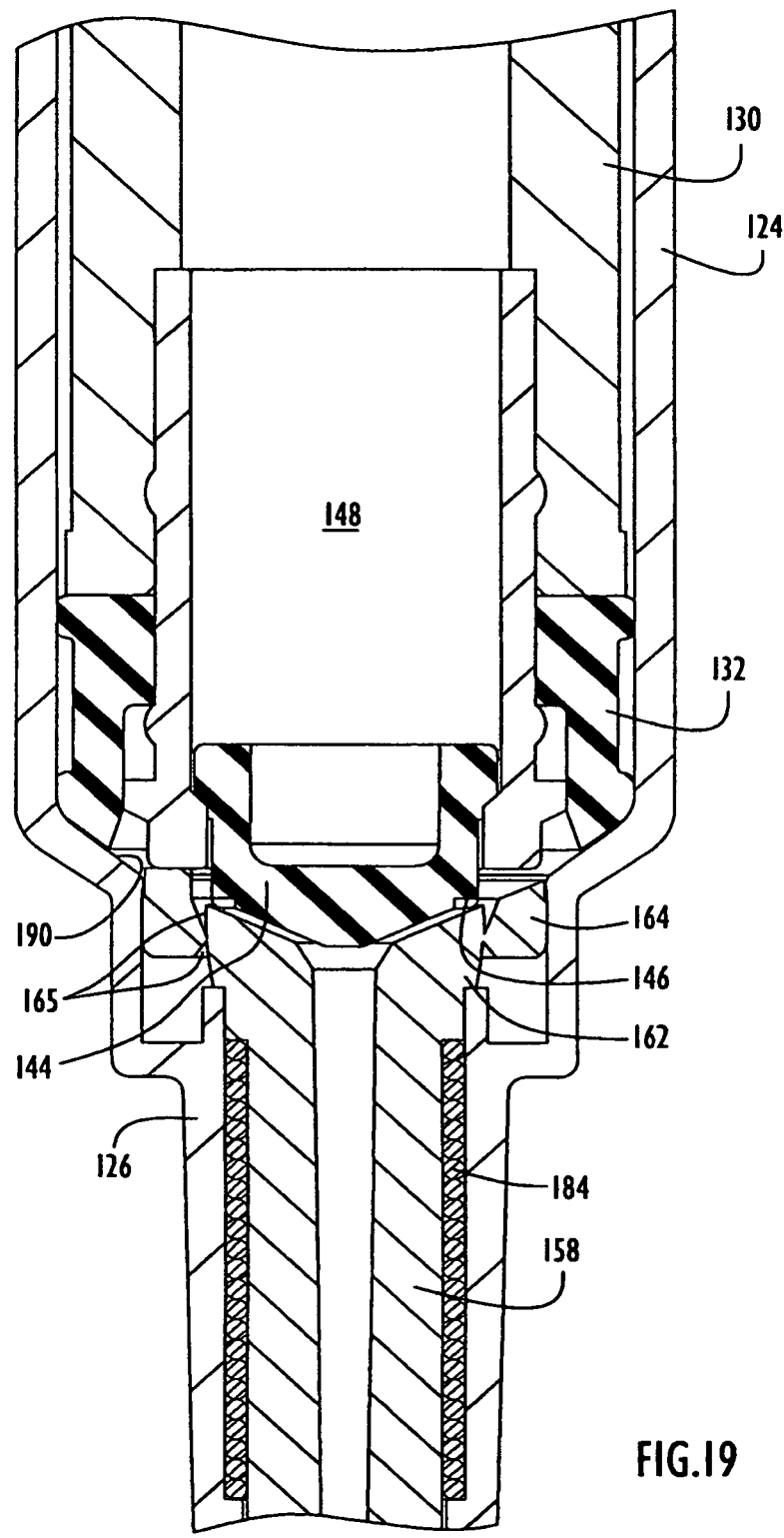
Figure 20:
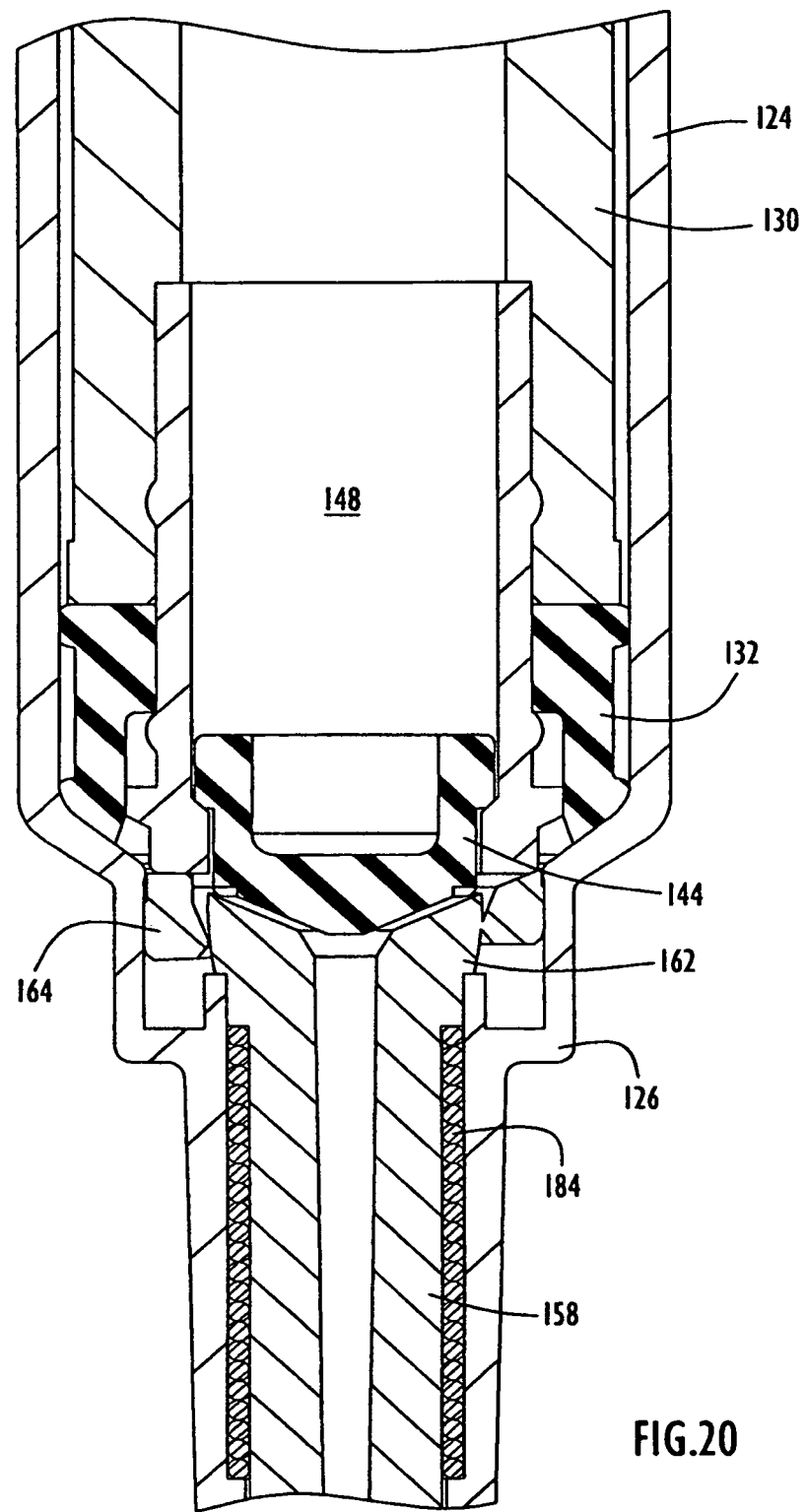

Referring to FIG. 17, plunger 130 includes a membrane or plug 144 disposed at a distal end of the plunger and that is frictionally held between interior wall portions of the plunger (e.g., a frictional engagement similar to that described above and depicted in FIG. 12). The plug 144 seals the hollow interior or retraction cavity 148 of plunger 130, with the frictional engagement between the plug and the plunger being suitable to maintain engagement of the plug with the plunger until retraction of the needle assembly occurs as described below. Alternatively, it is noted that the plunger membrane or plug can be secured at the distal end of the plunger in a snap tight fitting relationship (e.g., as in the embodiment depicted in FIG. 13) or in any other suitable manner.

As can be seen in FIG. 17, the distal end of plunger 130 includes an opening that communicates with retraction cavity 148 and into which plug 144 is secured. The interior annular wall at the distal end of the plunger includes an inwardly extending radial ledge 141. The diameter or transverse cross-section of the plunger opening, as defined at the ledge 141, is smaller than the diameter or transverse cross-section of the retraction cavity 148 that is defined within the plunger and lies beyond the ledge 141. Similarly, plug 144 includes an extending portion 147 that extends transversely from a proximal end of the plug. The extending portion 147 of the plug 144 is slightly larger in transverse cross-sectional dimension than the transverse cross-sectional dimension of the plunger opening defined at the ledge 141, so as to facilitate frictional contact between the ledge 141 and the extending portion 147 of the plug 144. The transverse cross-sectional dimensions of the extending portion 147 as well as the rest of the plug 144 are smaller than the transverse cross-sectional dimension of the retraction cavity 148 between the plunger ledge 141 and the proximal end of the plunger. Further, the transverse cross-sectional dimension of the remaining plug portion that extends between the extending portion 147 and the distal end of the plug 144 is slightly smaller than the transverse cross-sectional dimension of the plunger opening. Thus, upon axial displacement of the extending portion 147 of the plug 144 from the ledge 141 of the plunger 130 during retraction of the needle assembly, the frictional engagement between the plunger and the plug is released and the plug is free to move into the retraction cavity.

The plunger plug 144 includes a convex and frusto-conical surface 145 that extends toward the distal end of the barrel and engages with a generally complimentary, concave and frusto-conical cavity portion 159 of needle assembly 156 when the plunger is fully depressed into the barrel as described below. As noted in the previous embodiments described above, the end wall may alternatively be formed with any suitable outwardly or inwardly extending surface (e.g., conical, convex, V-shaped, multifaceted, etc.) or even a flat or planar surface as desired for a particular application. However, complimentary engaging surface features of the plunger plug and the needle assembly are preferred in order to minimize or eliminate open or "dead" space within the fluid cavity during removal of fluid from the fluid cavity.

At least one notch 146 is formed on the plug at the base of the frusto-conical surface. The notch 146 can extend around the periphery of the plug at the base of the frusto-conical surface or, alternatively, consist of a single notch or one or more spaced notch sections. The notch basically serves to provide a fluid flow path between the fluid cavity within the barrel and the fluid channel in the needle assembly when the plunger is substantially or completely engages with the needle assembly. In addition, the notched plunger plug minimizes or eliminates the potential for an increase or build-up of hydraulic pressure within the fluid cavity during movement of the plunger toward the needle assembly.

Needle assembly 156 includes a needle holder or stem 158 that connects with a syringe needle 160 and is affixed within the distal end extension 126 of the barrel such that the needle 160 extends from the distal end of the barrel prior to and during use. The needle stem 158 and needle 160 preferably releasably engage with each other via any suitable fluid tight engagement. In a preferred embodiment, the releasable engagement between the needle stem and the needle is a threaded engagement, where the needle stem includes a male threaded configuration and the needle includes a female threaded connector to releasably connect with the needle stem. This connection, which is depicted in FIGS. 14 and 17-20, differs from conventional syringe needle connections, such as Luer Lock configurations. In addition, this threaded configuration provides an easy, universal connection with needles of various gauges and types. However, it is noted that the needle can also be attached to the needle stem in any other suitable releasable or non-releasable manner.

A cavity 157 extends axially from a proximal end of the needle stem 158 to the connection point with the needle 160 in order to facilitate fluid communication between the needle and fluid cavity 150 within the barrel. In addition, cavity 157 includes a widened portion 159 at the proximal end of needle stem 158 that is frusto-conical in configuration and widens toward the proximal end of the barrel so as to be generally aligned and complimentary with the frusto-conical surface 145 of the plunger 130. As noted above, when the plunger is depressed toward the needle assembly, the frusto-conical surface 145 of plug 144 generally aligns and engages with widened portion 159. When the plunger plug is brought toward and fully engages widened portion 159 of the needle assembly, notch 146 defined on plug 144 ensures a fluid flow path exists between fluid cavity 150 and needle assembly cavity 157 and reduces or eliminates any build-up of hydraulic pressure within the fluid cavity.

The needle stem 158 further includes a radially extending flange 162 at its proximal end that is suitably dimensioned to engage with a step or ledge 121 disposed along an interior surface of the distal end extension 126 in order to prevent movement of the needle assembly distally beyond ledge 121 during depression of the plunger toward the distal end of the barrel.

A stem ring 164 is secured to and extends radially from the flange 162 of needle stem 158 to engage with the interior wall surface of distal end extension 126 of the barrel. The stem ring 164 is preferably formed or molded as a part of flange 162 and needle stem 158 and includes notched or scored sections 165 at the connection point of stem ring 164 and needle stem 158, where the scored sections are formed on opposing surfaces of both the needle stem flange and the stem ring. The scored sections 165 define a thin membrane or reduced material section that is torn or broken during operation of the syringe to facilitate retraction of needle assembly 156 in the manner described below. The stem ring 164 is preferably dimensioned to facilitate a partial sliding of a broken portion of the stem ring along the interior wall surface of the barrel when the plunger is depressed to engage with needle stem 158 as described below.

The diameter of the stem ring can be selected to be slightly smaller, the same size, or slightly larger than the diameter of the interior wall surface of distal end extension 126 at the location where the stem ring engages the barrel. In the present embodiment, the diameter of stem ring 164 is slightly larger in comparison to the diameter of the interior wall surface of the barrel that engages with the stem ring such that the stem ring is slightly compressed during engagement with the barrel and forms an effective fluid tight seal. The dimensions of the stem ring are further selected to provide a compression fit/fluid tight seal at the stem ring/barrel interior wall interface while facilitating a sliding of the stem ring with the barrel interior wall surface when the plunger is completely depressed within the barrel. Alternatively, it is noted that the stem ring can be connected directly to the barrel interior wall surface (e.g., via adhesive bonding, welding, etc.).

A radial protrusion or annular shoulder 166 is disposed along the interior surface and near the proximal end of the distal end extension 126 of the barrel. The shoulder 166 engages with stem ring 164 to prevent movement of the needle assembly toward the proximal end of the barrel while the stem ring remains attached with needle stem 158. A resilient member 184 (e.g., a coil spring) is disposed between the flange 162 of needle stem 158 and an interior ledge 186 disposed on the interior surface of the distal end extension 126 at a location between ledge 121 and the distal end of the barrel. When the needle assembly 156 is press fit into the distal end extension 126 of the barrel (as described below) such that stem ring 164 is extended distally beyond the radial protrusion 166 of the barrel, resilient member 184 is compressed to bias the needle assembly toward the proximal end of the barrel.

Figure 16:
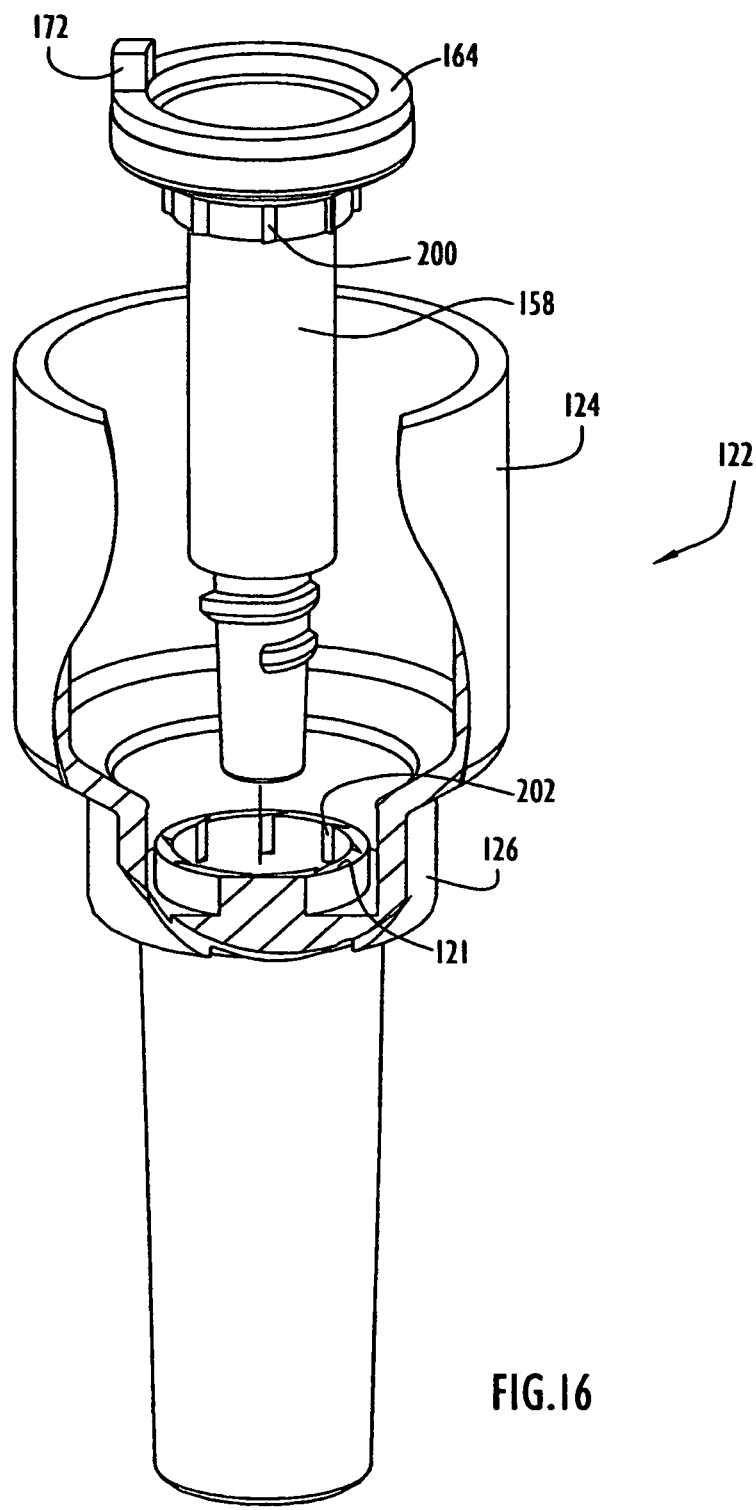
FIG. 16 is an exploded view in perspective of a portion of the syringe of FIG. 14 including the needle assembly and a distal end portion of the syringe barrel with a section removed to reveal the barrel interior.

Referring to FIG. 16, the needle stem and barrel include complimentary protrusions and grooves that facilitate easy assembly of the needle stem within the barrel and further limit or prevent any rotation of the needle stem with respect to the barrel after assembly and during operation of the syringe. In particular, needle stem 158 includes a set of protrusions or teeth 200 extending transversely from the outer surface of the needle stem at a location proximate the stem ring 164. The teeth are spaced around the periphery of the needle stem and are aligned to correspond with complimentary grooves 202 disposed along the interior barrel wall surface at the distal end extension 126 and at a location generally corresponding with the barrel ledge 121. As can be seen from FIG. 16, the teeth 200 and complimentary grooves 202 are configured to facilitate easy assembly of needle stem 150 within barrel 122, where the needle stem rotates as necessary upon insertion within the barrel until the teeth are appropriately aligned with the grooves and the needle stem is forced in place within the barrel distal end section. Once needle stem 158 is assembled within barrel 122 and the teeth 200 engage with the grooves 202, the needle stem is prevented from rotating with respect to the barrel during operation of the syringe (e.g., when attaching or removing a needle from the needle stem, and during retraction of the needle assembly within the plunger).

Alternatively, the syringe can be provided with other needle stem and barrel configurations that provide a locking engagement between the needle stem and the barrel. For example, the needle stem and barrel can include suitable complimentary protrusions and/or grooves to achieve a ratcheting or cam configuration that permits a selected degree of rotational movement of the needle stem within the barrel in one direction while limiting or preventing rotational movement of the needle stem within the barrel in an opposite direction.

As in the previous embodiments, the syringe 120 is designed so that complete depression of plunger 130 within barrel 122 facilitates a displacement of plunger plug 144 from the plunger and also a tearing or breaking away of the stem ring 164 from flange 162 of needle stem 158 to facilitate retraction of the needle stem and the needle 160 into the retraction cavity 148. In this embodiment, stem ring 164 of needle stem 158 includes at least one raised ridge 172 that extends from a proximal end of the needle stem and is configured to make initial contact with annular distal edge 178 of the plunger when the plunger is displaced within the barrel. While only one ridge 172 is depicted in FIGS. 17-20, it is noted that any selected number of ridges can be provided at any suitable locations and suitably spaced from each other along the proximal end of the needle stem that faces the plunger. In this embodiment, the ridge 172 serves a similar purpose as the angled annular surface with apex in the embodiment described above and depicted in FIGS. 1-6. However, the ridge 172 further permits air bubbles that may accumulate at one or more locations along the interior wall of the barrel after aspiration of fluid within the fluid cavity to be removed from the syringe with relative ease prior to forcing fluid from the syringe in an application (e.g., injection into a patient). The annular distal edge 178 of the plunger is generally planar in configuration. However, it is noted that the plunger distal end can include any one or more protrusions like the needle stem or, alternatively, have an angled contour to form an apex as in the embodiment described above and depicted in FIGS. 1-6.

Plunger resilient seal 132 is further designed and suitably dimensioned and positioned around the plunger proximate the plunger distal end such that, upon complete depression of the plunger within the barrel, a distal end of the resilient seal engages and compresses slightly against a narrowing portion 190 of the interior barrel wall that defines a transition between main body portion 124 and distal end extension 126. The resilient seal does not slide with respect to the plunger, but rather compresses slightly against the barrel wall narrowing portion at the end of the plunger stroke that initiates needle retraction, and this serves to further minimize or eliminate "dead" space within the fluid cavity 150 as well as to displace any residual fluid from the fluid cavity into needle stem cavity 157.

The needle stem can be assembled within the syringe such that the ridge (or ridges) is aligned in any selected orientation with respect to the plunger distal end. The stem ring ridge(s), plunger and annular distal end of the plunger and needle stem are suitably dimensioned in the longitudinal direction of the syringe and further suitably aligned with each other to facilitate engagement of stem ring ridge(s) 172 and/or other proximal end surface portions of stem ring 164 with annular distal edge 178 of the plunger and plunger plug 144 with needle stem 158 upon complete depression of the plunger, which in turn facilitates a tearing or breakage of stem ring 164 from needle stem flange 158 at the scored sections 165 and a forcing of plunger plug 144 from its frictional engagement with plunger ledge 141 to initiate retraction of needle assembly 56 along with the plunger plug into retraction cavity 48 of the plunger.

Assembly of the syringe is achieved in a similar manner as the other syringe embodiments described above. Resilient member 184 and then needle assembly 156 (with or without the needle 160) are first inserted into opening 123 at the proximal end of barrel 122, through main body portion 124 and into the distal end extension 126. As the stem ring 164 of needle stem 158 encounters annular shoulder 166 of the barrel, the stem ring is compressed slightly and forced distally beyond the shoulder 166 in a snap-fit engagement. Once stem ring 164 is forced distally beyond shoulder 166, the needle assembly 156 is locked in place within the distal end extension 126, and resilient member 184 is compressed to bias the needle assembly proximally within the syringe. The stem ring 164 remains compressed to a selected degree between flange 162 and the barrel interior wall surface in this locked configuration and provides an effective fluid tight seal at its compressed fit contact point with the barrel.

Plunger 130 is assembled by inserting plunger plug 144 into the plunger such that the extending portion 147 of the plug frictionally engages plunger ledge 141 located at the open distal end of the plunger and a distal portion of the plunger plug (including plug surface 145 and notch 146) extends from the plunger. The plunger plug can be inserted directly into the open distal end of the plunger to its frictional fitting position. In the embodiment depicted in FIGS. 14-21, the proximal end of the plunger, including thumb pad 138 and flange 139, is a single molded or formed part. Alternatively, in embodiments where the plunger flange and thumb cap are separate from the rest of the plunger (as in the embodiment described below and depicted in FIG. 22), the plunger plug can first be inserted through an open proximal end of the plunger and pushed into its frictional fitting position prior to sealing this open end with the flange and thumb pad.

After assembly of the plunger, the plunger is inserted into opening 123 of barrel 122 and is axially displaced a suitable distance to facilitate use of the syringe. The needle 160 may be connected with needle stem 158 prior to insertion of the needle assembly into barrel 122 (e.g., via the threaded engagement as depicted in FIG. 16). Alternatively, needle 160 may be connected with the connecting portion of needle stem 158 after securing the needle stem within the barrel. Once secured, needle 160 protrudes from the opening at the distal end of the barrel after assembly to facilitate use of the syringe.

In operation, the distal end of the plunger is displaced a suitable distance toward the proximal end of the barrel to draw fluid from needle 160 into fluid cavity 150. Upon injection of the needle into an injection site, the plunger is then depressed toward the distal end of the barrel to force fluid from cavity 150 and through needle 160. Referring to FIGS. 17-20, as the plunger is further depressed within the barrel, the frusto-conical surface 145 of plunger plug 144 moves into the widened portion 159 of central cavity 157 of needle stem 158 to force any remaining fluid through the needle prior to retraction (thus reducing "dead" space between the engaging portions of the plunger and needle assembly). The notch 146 on the plunger plug provides a fluid channel for fluid to continue to flow into central cavity 157 even when plunger surface 145 is substantially in contact with the widened cavity portion 159. In addition, ridge(s) 172 of needle stem 158 initially engages a portion of annular distal edge 178 of the plunger to initiate a tearing or breaking away of stem ring 164 from needle stem 158 along the scored sections 165. Approximately contemporaneously, surface 145 of plunger plug 144 engages needle stem 158 within the widened cavity portion 159, and such continued depression of the plunger toward the needle assembly overcomes the frictional force holding the plunger plug within the plunger, forcing the plunger plug toward the proximal end of the plunger and into retraction cavity 148.

Complete depression of the plunger within the barrel further forces plunger annular distal edge 178 against other surface portions of stem ring 164, causing the portion of the stem ring that has already broken away from flange 62 to slide distally a short distance along the interior wall of the barrel so as to become oriented at a slight angle with respect to the central axis of needle stem 158. In addition, the portion of the stem ring that has not broken away is prevented from moving distally until it has become broken away from the needle stem. This sliding of the broken portion of the stem ring 164 along the interior wall of the barrel, in combination with the continued pressure applied by the fully depressed plunger to the stem ring, results in a progressive tearing or breakage of the stem ring in both directions along scored sections 165 until the stem ring is fully separated from tab 162. In addition, the forced engagement of plunger plug 144 with needle stem 158 results in further movement of the plunger plug from its frictional engagement with the distal end ledge 141 of the plunger, resulting in dislodging of the plunger plug from the plunger. Plunger resilient seal 132 compresses slightly against the narrowed portion 190 of the barrel interior wall to force residual fluid into the needle assembly, while plunger plug notch 146 provides a fluid flow path for such fluid when plunger surface 145 engages with needle stem 158 within widened cavity portion 159.

The design of the syringe can be configured such that the stem ring 164 is completely separated from needle stem 158 immediately prior to, substantially simultaneously with, or immediately after the complete dislodging of plunger plug 144 from the plunger. As shown in the series of FIGS. 17-20, the initial dislodging and axial displacement of plunger plug 144 begins just prior to initial contact between stem ring ridge 172 and plunger distal edge 178 and partial breakage of stem ring 164 from needle stem tab 162. However, the syringe can also be designed such that initial and partial breakage of the stem ring occurs prior to any initial dislodging and axial displacement of the plunger plug. Once complete separation of the stem ring from the tab of the needle stem and at least a partial dislodging of the frictional engagement between the plunger plug and the plunger is achieved, resilient member 184 forces needle stem 158 and needle 160, along with plunger plug 144, proximally into the retraction cavity 148 within the plunger.

Figure 21:
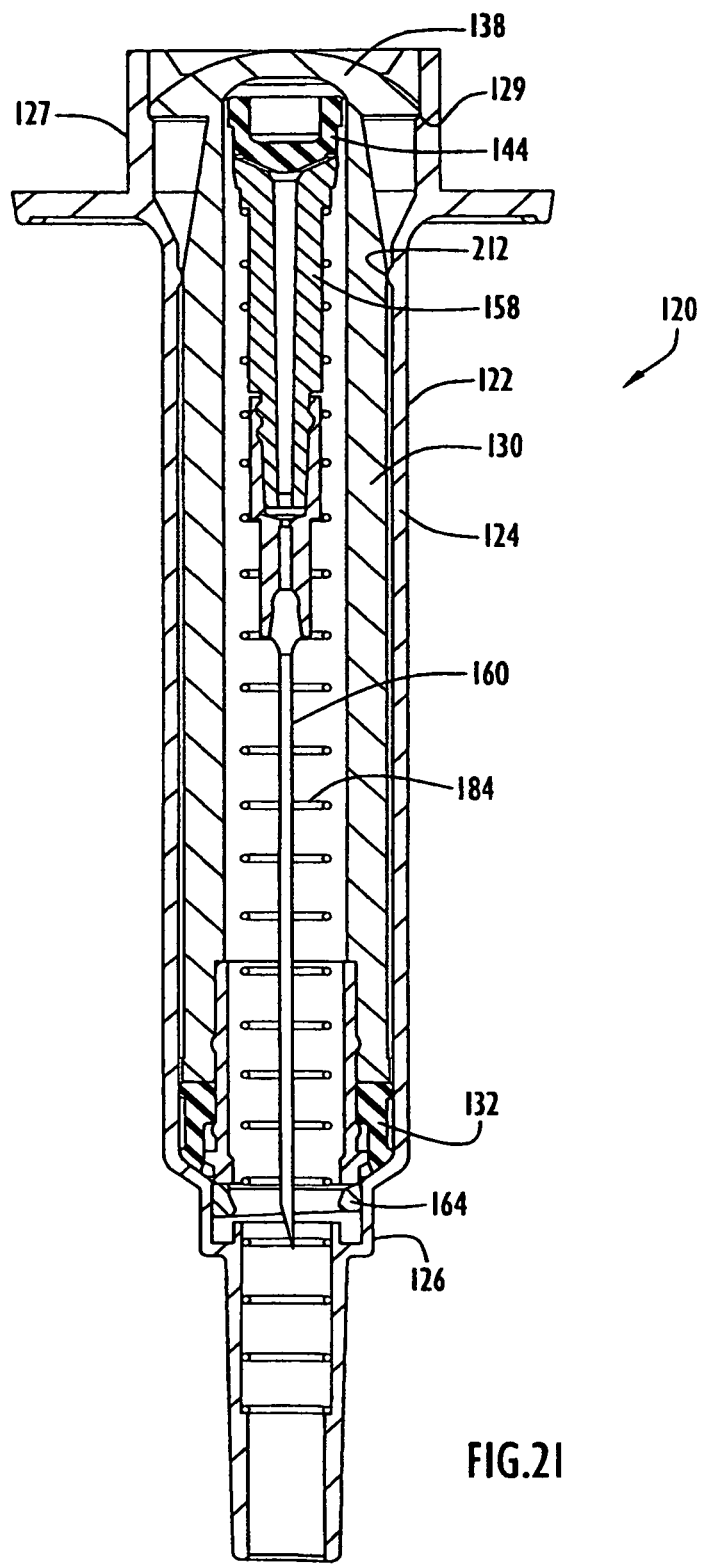
FIG. 21 is a side view in cross-section of the syringe of FIG. 14 with the needle fully retracted into the syringe after use.

As can be seen from FIG. 21, when plunger 130 has been fully depressed within barrel 122 and retraction of needle assembly 156 has occurred, flange 139 of the plunger extends slightly into the extended barrel portion 127 and is locked within annular groove 129. In this locked position, removal of the plunger from the barrel is prevented.

Figure 22:
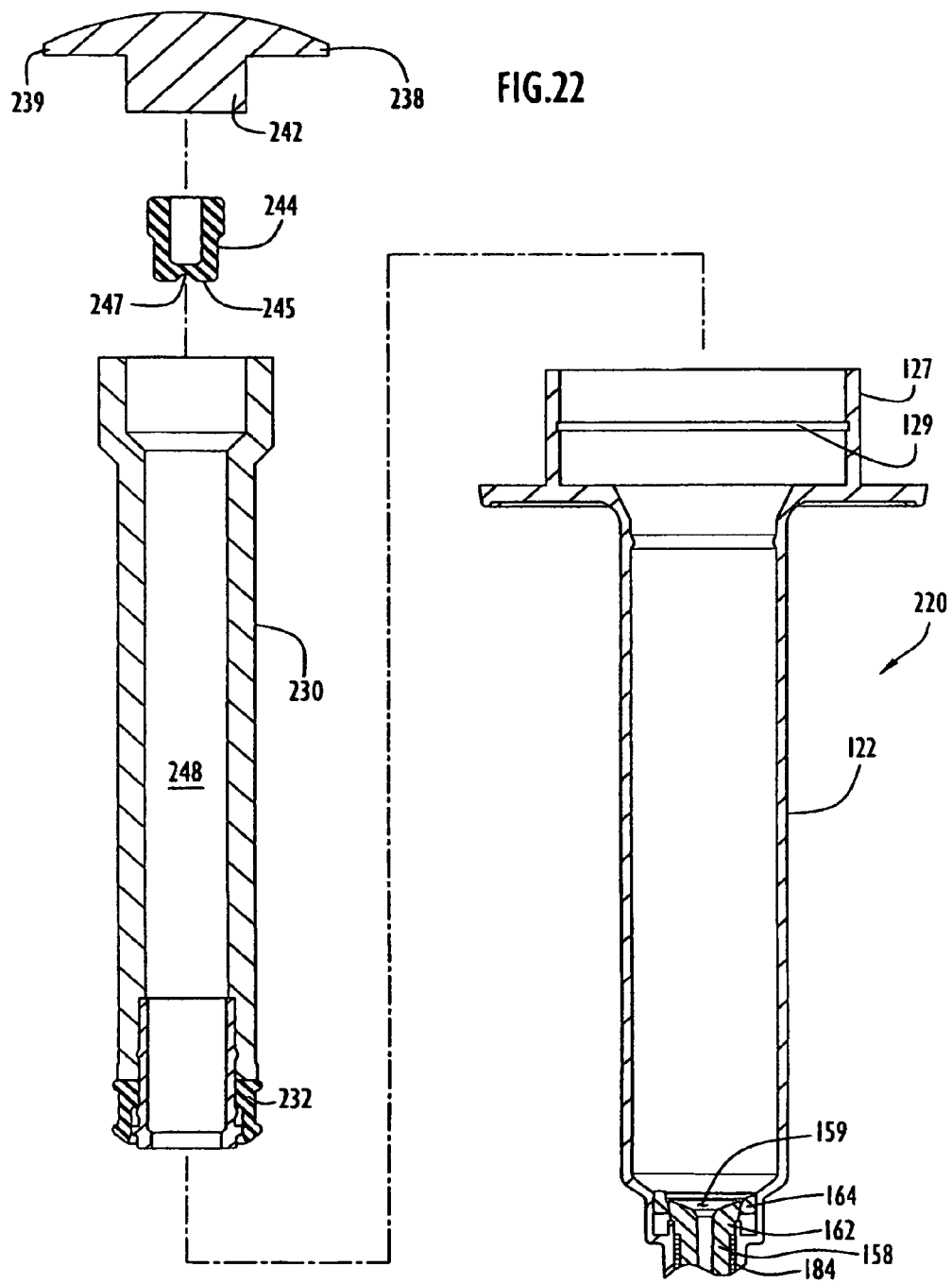
FIG. 22 is a partially exploded side view in cross-section of a portion of another embodiment of a syringe in accordance with the present invention.

As noted above, the syringe of FIGS. 14-21 can be modified such that the plunger includes a thumb pad or cap that is a separate part or component from the main plunger body. An exemplary embodiment is depicted in FIG. 22. Syringe 220 includes a barrel 122 and needle assembly that are substantially similar to the same parts or components as described above and depicted in FIGS. 14-21. The plunger includes a hollow main body portion 230 including a resilient seal 232 disposed near the distal end of the main body portion and that is substantially similar to the plunger seal described above in the previous embodiment. A thumb pad or cap 238 includes an insert 242 that is suitably dimensioned to fit within and frictionally engage with an opening defined at the proximal end of the main body 230. The thumb cap further includes a flange 239 that is of greater transverse cross-sectional dimension than the insert 242 and abuts the proximal end of the plunger upon engagement of the insert within the plunger. The flange 239 further provides a gripping surface for the plunger during use of the syringe as well as a tapered edge that engages with annular groove 129 in the extended barrel portion 127 when the plunger is fully depressed and locked within the barrel.

A plunger plug 244 is frictionally held within an opening at the distal end of the plunger in a substantially similar manner as described in the previous embodiment. However, plug 244 differs from the plunger plug of the previous embodiment in that it includes a generally flat or planar distal end surface 245 with a notch 247 disposed along this surface. The planar surface 245 of plug 244 engages with a portion of the widened cavity portion 159 of the needle stem 158, while notch 247 serves to minimize hydraulic pressure build-up within the syringe cavity during axial movement of the plunger toward the needle assembly to initiate needle retraction.

The design of the plunger in this manner allows easy assembly of the plunger plug. In particular, plug 244 can be inserted within plunger main body 230 at the open proximal end prior to connection of thumb cap 238 with the main body. The plunger plug can be forced through the plunger retraction cavity 248 into frictional engagement at the open distal end of the plunger main body, followed by insertion of thumb cap insert 242 into the opening at the plunger proximal end. Thumb cap 238 can be firmly secured to main body 230 in any suitable manner (e.g., via an adhesive, welding, etc.) to prevent removal of the thumb cap from the main body after assembly. Once the plunger is assembled within barrel 122, the syringe 220 operates in a substantially similar manner as the previous embodiment described above and depicted in FIGS. 14-21 to facilitate a single use and needle retraction.

The present invention is not limited to the syringe embodiments described above and can include additional features. For example, the syringe can further include color coding for the needle holder and matching needle cover to correspond with a particular application. In particular, matching color codes can be selected that are in compliance with ISO 6009 and/or any other selected color coding standards.

The resilient seal of the plunger can also be modified such that a portion of the seal extends over at least part of the distal end of the plunger. The resilient seal can further include an opening to hold and frictionally retain a portion of a plunger plug as described in some of the previous embodiments. Providing a resilient seal that extends over the distal end of the plunger in this manner further reduces potential "dead" space that may otherwise exist within the fluid cavity of the syringe.

Figure 23:
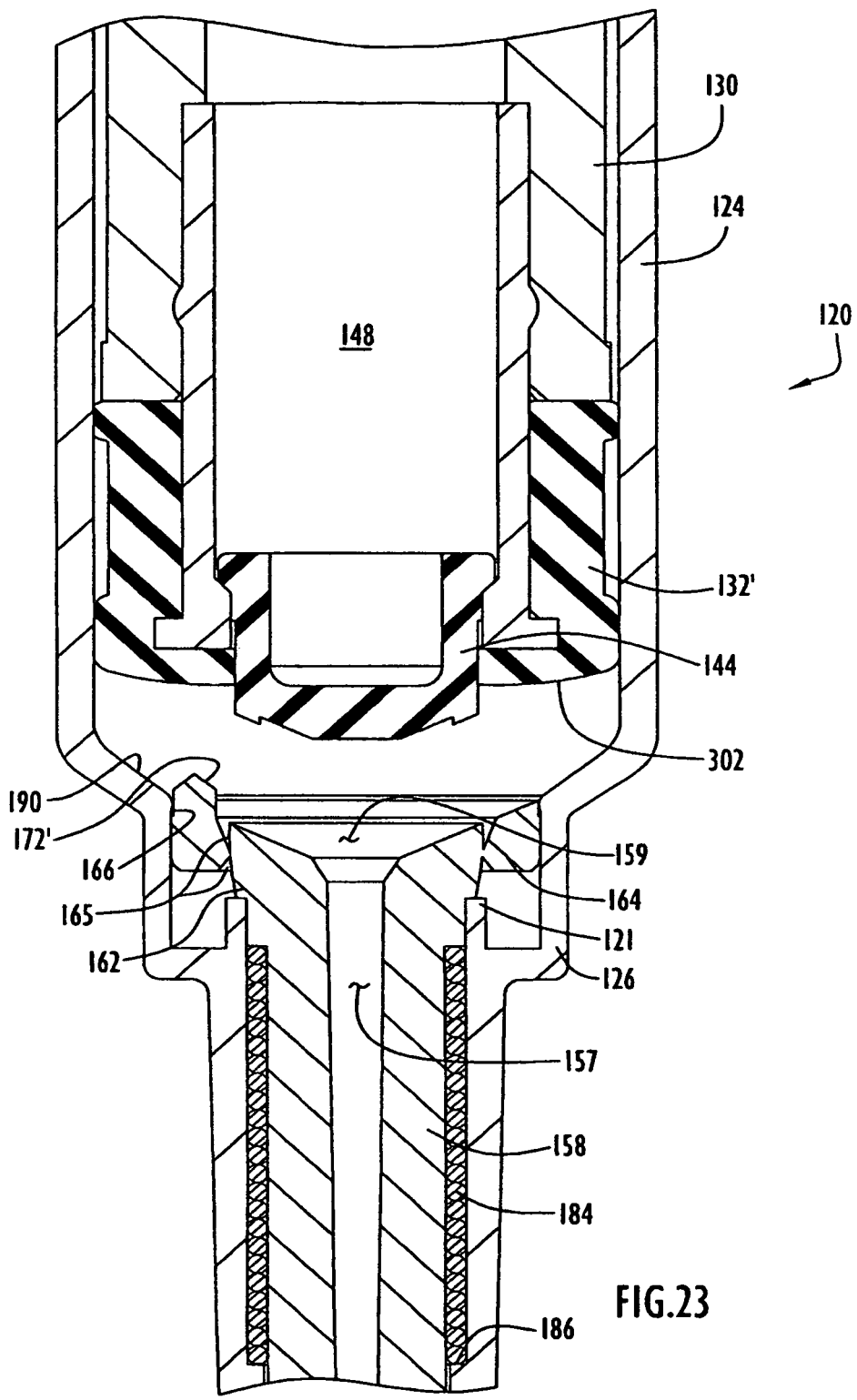
FIG. 23 is a partial side view in cross-section of yet another embodiment of a syringe in accordance with the present invention.

An exemplary embodiment of a syringe including a plunger resilient seal that extends around the plunger distal end is depicted in FIG. 23. The syringe embodiment of FIG. 23 is similar in design and operation to the syringe described above and depicted in FIGS. 14-21, with the exception that plunger resilient seal 132' includes a distal end 302 that extends over the distal end of plunger 130. The distal end 302 of the resilient seal 132' further includes an opening that is suitably dimensioned to receive and frictionally engage plunger plug 144. In this embodiment, the plunger plug frictionally engages with both the resilient seal and the distal end ledge of the plunger, and the frictional engagement of the plunger plug with the resilient seal and plunger is overcome upon complete movement or depression of the plunger into the barrel during needle retraction. The opening in the plunger seal is also sufficiently dimensioned to permit movement of the needle stem with needle through the plunger seal during needle retraction.

The syringe depicted in FIG. 23 could be modified such that the plunger plug frictionally engages with only one of the resilient seal and the plunger. In another modification of the syringe of FIG. 23, stem ring ridge 172' includes a pointed or sharp edge that faces the plunger distal end and engages with the resilient seal distal end 302 upon complete movement of the plunger into the barrel. The resilient seal 132' substantially minimizes or prevents the existence of "dead" space within the fluid cavity when the plunger is fully depressed within the barrel.

As noted above, the plunger plug can also be held in a snap-tight or releasable locking configuration with respect to one or more portions of the plunger, where the snap-tight fitting arrangement is overcome upon full or complete depression of the plunger within the barrel such that the plunger plug can move with the needle stem into the retraction cavity. The snap-tight fit or releasable locking arrangement can be achieved by providing any suitable number (e.g., one or more) of protrusions and/or complimentary grooves on one or both of the plunger and plunger plug.

Figure 24:
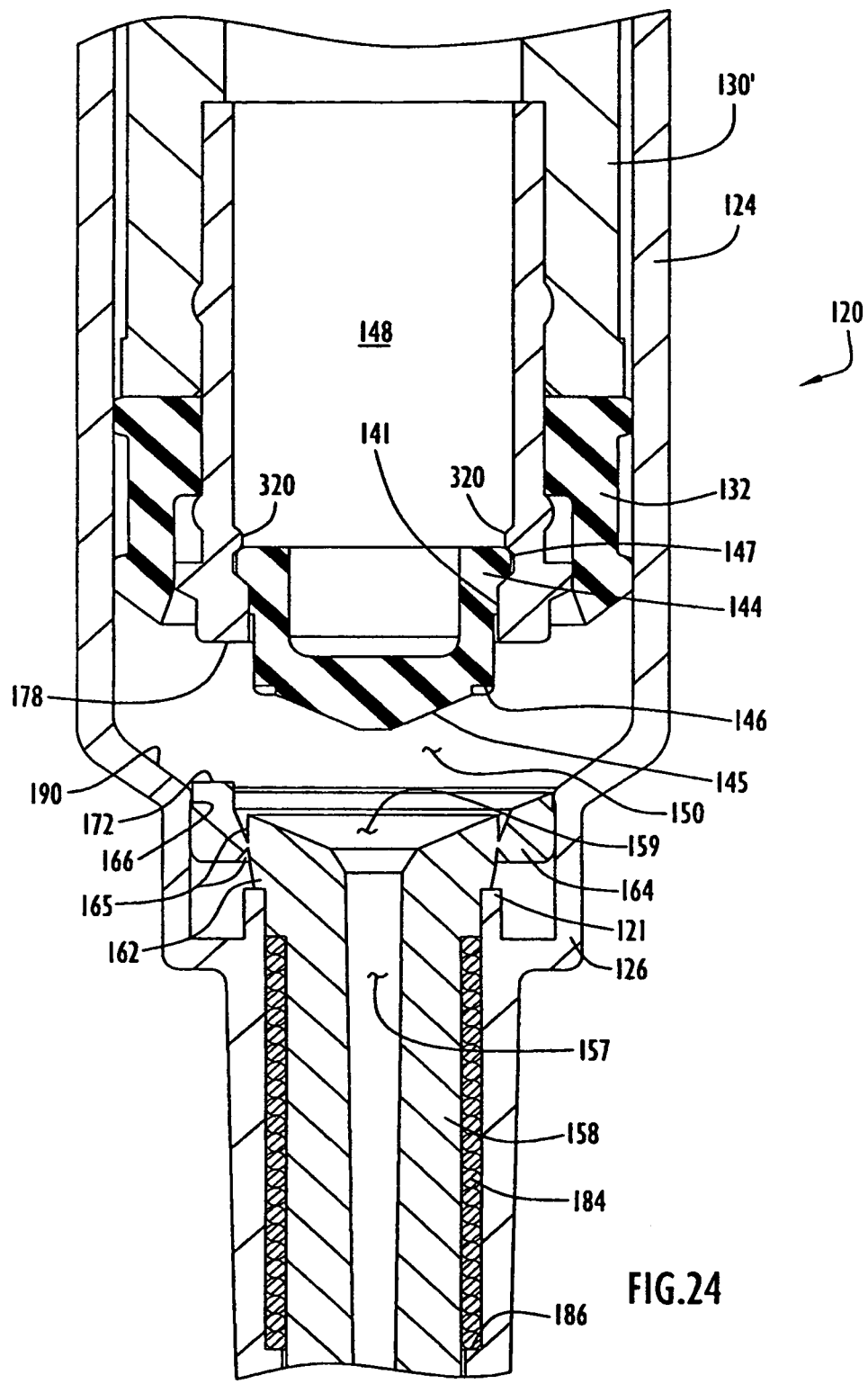
FIG. 24 is a partial side view in cross-section of still another embodiment of a syringe in accordance with the present invention.

Referring to FIG. 24, the plunger of the syringe described above and depicted in FIGS. 14-21 is modified to include one or more protrusions that serve to lock the plunger plug in place during use and prior to needle retraction. In particular, plunger 130' includes an inwardly extending radial protrusion 320 disposed near the plunger distal end and proximally from inwardly extending radial ledge 141. When plunger plug 144 is secured within the distal end opening of the plunger, protrusion 320 abuts the extending portion 147 of the plunger plug and prevents movement of the plunger plug proximally within the retraction cavity during aspiration of fluid into and ejection of fluid from the syringe. However, upon complete depression or movement of the plunger within the barrel, the contact between the plunger plug and the needle stem forces the plug extending portion 147 beyond ridge 320, which allows the plunger plug to retract into retraction cavity 148 along with the needle stem and needle.

Figure 25:
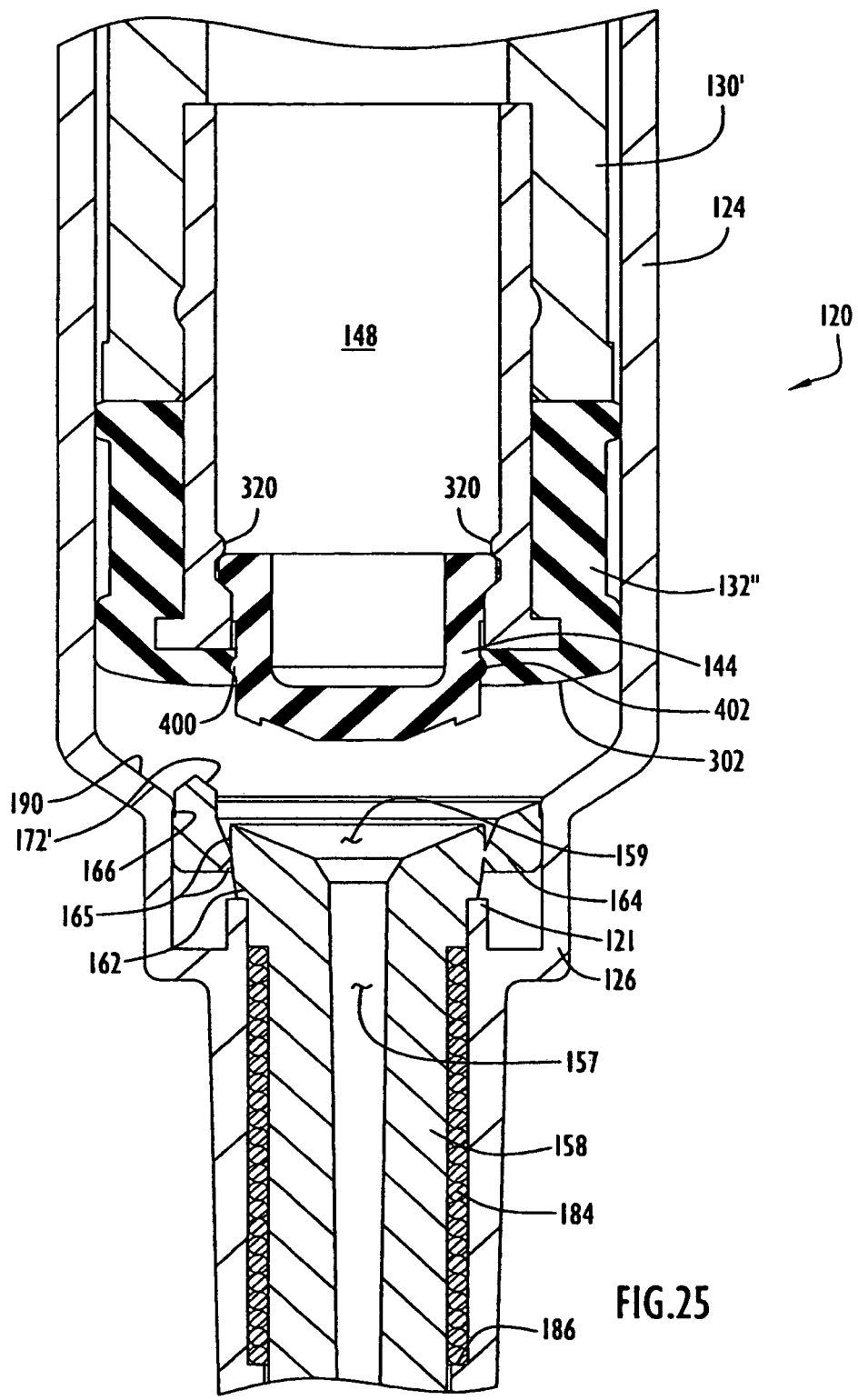
FIG. 25 is a partial side view in cross-section of a further embodiment of a syringe in accordance with the present invention.

A similar embodiment is depicted in FIG. 25, in which the syringe of FIG. 23 is modified to include snap-fit or locking elements between the plunger plug and plunger. In particular, plunger 130' includes an inwardly extending radial protrusion 320 as previously described in the embodiment of FIG. 24. In addition, plunger plug 144' includes an outwardly extending radial bump or protrusion 400 that is configured to engage with a corresponding radial groove 402 disposed along an inward surface of resilient seal 132". The protrusion 400 engages with the groove 402 in a snap-fit locking arrangement to further prevent movement of the plunger plug with respect to the plunger until the plug engages the needle stem and is forced into the retraction cavity 148 along with the needle stem.

The syringe can further be designed with a needle locking feature to prevent inadvertent removal or release of the syringe needle from the needle stem or holder during use of the syringe. For example, in embodiments in which the needle is removably secured to the needle holder via a threaded engagement, the needle locking feature prevents inadvertent separation between the needle and the needle holder that may otherwise occur due to inadvertent twisting of the needle with respect to the needle holder when the needle cover or sheath is removed from the syringe and/or other twisting forces are applied to the needle by the user during syringe operation.

Figure 26A:
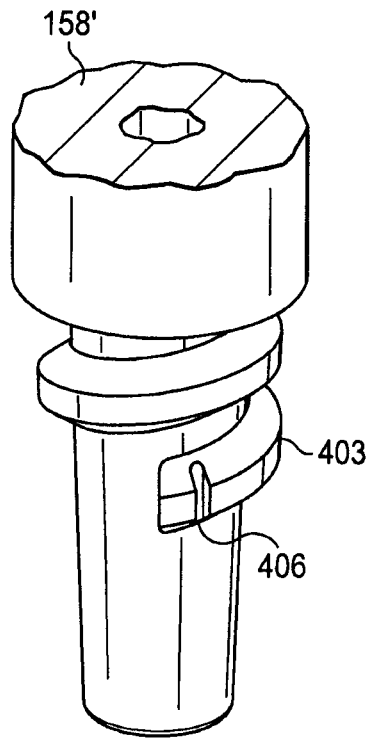
FIG. 26A is a partial side view of a needle holder for a syringe in accordance with another embodiment of the present invention.
Figure 26B:
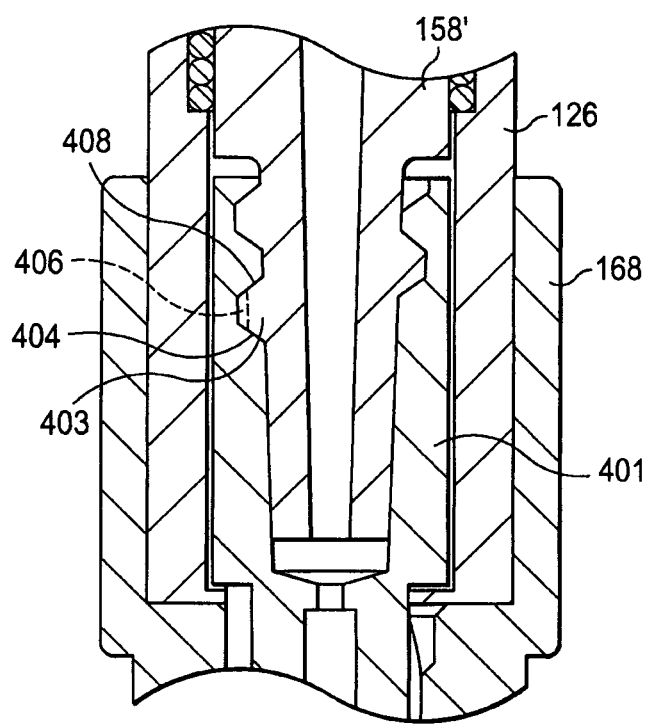
FIG. 26B is a partial side view in cross-section of a syringe embodiment in accordance with the present invention and including the needle holder of FIG. 26A.

The needle locking feature can be implemented in the syringe described above and depicted in FIGS. 14-21 by providing at least one protrusion and at least one corresponding locking groove on the male and female threaded connectors of the needle holder and needle. Referring to FIGS. 26A and 26B, a modified embodiment of the syringe of FIGS. 14-21 is depicted, where needle stem 158' of the needle assembly includes a male threaded configuration that releasably connects with a corresponding female threaded connector 400 for needle 160. As can be seen from FIG. 26A, the male threaded portion of needle stem 158' extends radially from and winds around the stem. The male threaded portion further includes a starting or lead-in portion 403 that ramps radially outward from the needle stem until it achieves the final radial dimension of the male threaded portion. A groove or notch 406 is disposed on lead-in portion 403 of the needle stem male threaded portion, where the notch 406 extends transversely across the lead-in portion. A corresponding bump or protrusion 408 is disposed on a female threaded portion 404 of connector 400.

The notch and protrusion are suitably dimensioned and aligned on each of the needle assembly and female threaded connector for the needle such that, upon substantially complete engagement of the male threaded needle assembly with the female threaded connector for the needle, protrusion 408 slides into and engages with notch 406 to provide a releasable locking engagement between the needle assembly and the needle. In particular, the protrusion 408 rides over the initial ramping section of lead-in portion 402 until it encounters and engages with notch 406. This locking engagement resists slight and inadvertent torque or twisting forces applied to the needle (e.g., during removal of sheath 168 from the syringe) and can be overcome upon applying a sufficient twisting force to the needle with respect to the needle assembly.

Optionally, the protrusion and/or groove can include multifaceted and/or ramped surfaces to facilitate a ratchet-like locking action, where the twisting of the needle with respect to the needle assembly in a first direction (e.g., a clockwise direction) so as to engage the male and female threaded connections is facilitated with relative ease to lock the protrusion with the groove, while the twisting of the needle with respect to the needle assembly in a second direction that opposes the first direction (e.g., a counter-clockwise direction) is resisted by the engagement of the protrusion in the groove. In addition, the sheath may also be designed to prevent twisting of the sheath with respect to the syringe barrel during removal of the sheath, so as to further minimize or prevent inadvertent twisting of the needle with respect to the needle assembly.

A syringe in accordance with the present invention can also be configured for use in other, needle-free applications (i.e., applications that do not include the use of needles). For example, a syringe of the present invention can be configured with a suitable connector to connect directly with an intravenous (IV) fluid line for injection of fluid from the syringe into the IV line. The retraction of the needle stem would prevent further use of the syringe after a single fluid injection.

While the invention has been described in detail and with reference to a specific embodiment thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

The invention claimed is:

1. A syringe, comprising:
 a hollow barrel having a proximal opening, a distal end including a distal end opening and a fluid chamber defined therebetween;
 a hollow plunger having a cavity and extending into the barrel via the proximal opening and axially movable within the barrel toward and away from the distal end opening;
 a needle assembly coupled to the barrel distal end and including a needle stem;
 a needle system including a needle having a needle connector configured to be selectively attached to the needle stem, the needle stem and needle each configured to be retracted into the barrel; and
 wherein the needle system is configured such that it is restricted from providing an axial force to the needle stem during attachment of the needle connector to the needle stem to prevent unintended retraction of the needle stem into the barrel during attachment of the needle connector to the needle stem.

2. The syringe as specified in claim 1 wherein the needle stem and the needle connector each include securing sections configured to mutually engage with each other such that different gauge said needles can be selectively attached to the needle stem.

3. The syringe as specified in claim 2 wherein the securing sections comprise threaded portions configured to secure upon rotation of the needle connector with respect to the needle stem.

4. The syringe as specified in claim 1 wherein the needle system includes a protective sheath configured to engage about the barrel distal end during attachment of the needle connector to the needle stem before the needle connector can axially engage the needle stem.

5. The syringe as specified in claim 1 wherein the needle system includes a sheath configured to abut the barrel distal end to prevent the needle connector from providing an axial force to the needle stem during attachment of the needle connector to the needle stem.

6. The syringe as specified in claim 1 wherein the needle assembly includes a recess configured to receive the barrel distal end.

7. The syringe as specified in claim 6 wherein the barrel distal end comprises an annular collar, and the recess is configured to receive the barrel distal end collar.

8. The syringe as specified in claim 7 wherein the recess is at least partly annular.

9. The syringe as specified in claim 4 wherein the protective sheath is configured to allow rotation of the needle connector about the needle stem therein.

10. The syringe as specified in claim 5 wherein the sheath comprises an annular collar configured to engage the barrel distal end.

11. The syringe as specified in claim 4 wherein the protective sheath includes a recess configured to receive the barrel distal end.

12. The syringe as specified in claim 11 wherein the barrel distal end comprises an annular collar, and the recess is configured to receive the barrel distal end collar.

13. The syringe as specified in claim 12 wherein the recess is at least partially annular.

14. The syringe as specified in claim 4 wherein the sheath is coupled to the needle connector.

15. The syringe as specified in claim 14 wherein the sheath is configured to be selectively removable from the needle connector.

16. The syringe as specified in claim 1 wherein the needle stem further comprises a retaining member configured to couple the needle stem to the barrel, the retaining member configured to break away during retraction of the needle stem into the barrel.

17. The syringe as specified in claim 16 wherein the needle assembly is configured such that it is restricted from receiving an axial force sufficient to break the retaining member during attachment of the needle connector to the needle stem to prevent unintended retraction of the needle stem into the barrel during attachment.

18. The syringe as specified in claim 16 wherein the needle stem and the needle connector each include securing sections configured to mutually engage with each other such that the needle connector can be selectively attached to the needle stem.

19. The syringe as specified in claim 17 wherein the retaining member has a scored section.

20. The syringe as specified in claim 19 wherein the retaining member comprises a ring.

* * * * *

UNITED STATES PATENT AND TRADEMARK OFFICE
CERTIFICATE OF CORRECTION

PATENT NO.        : 8,684,966 B2                                    Page 1 of 1
APPLICATION NO.   : 12/924424
DATED             : April 1, 2014
INVENTOR(S)       : Janek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this
Thirtieth Day of May, 2017

Michelle K. Lee
*Director of the United States Patent and Trademark Office*